United States Patent
Fuks et al.

(10) Patent No.: US 8,114,610 B2
(45) Date of Patent: Feb. 14, 2012

(54) DEVICES AND METHODS FOR DETECTING AMNIOTIC FLUID IN VAGINAL SECRETIONS

(75) Inventors: Boris Fuks, Billerica, MA (US); Dmitrii Dmitrievich Petrunin, Moscow (RU); Evgeny I. Zaraisky, Moscow (RU); Marina Nikolayevna Boltovskaya, Moscow (RU); Svetlana Vladimirovna Nazimova, Moscow (RU); Nelly Andronikovna Starosvetskaya, Moscow (RU); Alexandr Konstantinov, Nashua, NH (US); Margarita Igorevna Marshiskaia, Moscow (RU)

(73) Assignee: N-Dia, Inc., Boston, MA (US)

( * ) Notice: Subject to any disclaimer, the term of this patent is extended or adjusted under 35 U.S.C. 154(b) by 0 days.

(21) Appl. No.: 12/722,369

(22) Filed: Mar. 11, 2010

(65) Prior Publication Data

US 2010/0311190 A1     Dec. 9, 2010

Related U.S. Application Data

(63) Continuation of application No. 10/524,668, filed as application No. PCT/US03/25125 on Aug. 12, 2003, now Pat. No. 7,709,272.

(60) Provisional application No. 60/403,407, filed on Aug. 13, 2002.

(51) Int. Cl.
*G01N 33/53* (2006.01)
*G01N 33/543* (2006.01)

(52) U.S. Cl. .................. 435/7.1; 435/287.7; 435/287.9; 435/805; 435/970; 436/514; 436/518; 436/164; 436/169; 436/805; 436/807; 436/810; 436/815

(58) Field of Classification Search .................. None
See application file for complete search history.

(56) References Cited

U.S. PATENT DOCUMENTS

| | | |
|---|---|---|
| 3,817,837 A | 6/1974 | Rubenstein et al. |
| 4,313,734 A | 2/1982 | Leuvering |
| 4,366,241 A | 12/1982 | Tom et al. |
| 4,373,932 A | 2/1983 | Gribnau et al. |
| 4,632,901 A | 12/1986 | Valkirs et al. |
| 4,703,017 A | 10/1987 | Campbell et al. |
| 4,770,853 A | 9/1988 | Bernstein |
| 4,806,312 A | 2/1989 | Greenquist |
| 4,810,658 A | 3/1989 | Shanks et al. |
| 4,857,453 A | 8/1989 | Ullman et al. |
| 4,906,439 A | 3/1990 | Grenner |
| 4,918,025 A | 4/1990 | Grenner |

(Continued)

FOREIGN PATENT DOCUMENTS

EP            0143574         6/1985

(Continued)

OTHER PUBLICATIONS

Canadian IPO Search Report dated Apr. 14, 2010 for Canadian counterpart Application Serial No. 2,533,915 filed Aug. 12, 2003.

(Continued)

*Primary Examiner* — Chris L Chin
(74) *Attorney, Agent, or Firm* — Fish & Richardson P.C.

(57) ABSTRACT

The present invention relates to a diagnostic method for the detection of small quantities of amniotic fluid in the vagina. More specifically, the invention relates to the detection of PAMG-1 in the vagina using anti-PAMG-1 antibodies.

8 Claims, 1 Drawing Sheet

U.S. PATENT DOCUMENTS

| | | | |
|---|---|---|---|
| 4,952,517 | A | 8/1990 | Bahar |
| 4,978,503 | A | 12/1990 | Shanks et al. |
| 4,981,768 | A | 1/1991 | Monbaliu et al. |
| 5,030,558 | A | 7/1991 | Litman et al. |
| 5,037,735 | A | 8/1991 | Khanna et al. |
| 5,051,237 | A | 9/1991 | Grenner et al. |
| 5,073,484 | A | 12/1991 | Swanson et al. |
| 5,114,673 | A | 5/1992 | Berger et al. |
| 5,137,808 | A | 8/1992 | Ullman et al. |
| 5,138,868 | A | 8/1992 | Long |
| 5,141,871 | A | 8/1992 | Kureshy et al. |
| 5,147,609 | A | 9/1992 | Grenner |
| 5,156,952 | A | 10/1992 | Litman et al. |
| 5,186,897 | A | 2/1993 | Eason et al. |
| 5,252,459 | A | 10/1993 | Tarcha et al. |
| 5,284,749 | A | 2/1994 | Crowley et al. |
| 5,308,775 | A | 5/1994 | Donovan et al. |
| 5,352,582 | A | 10/1994 | Lichtenwalter et al. |
| 5,554,504 | A | 9/1996 | Rutanen |
| 5,597,700 | A | 1/1997 | Konstantinov et al. |
| 5,602,040 | A | 2/1997 | May et al. |
| 5,622,871 | A | 4/1997 | May et al. |
| 5,654,162 | A | 8/1997 | Guire et al. |
| 5,712,172 | A | 1/1998 | Huang et al. |
| 5,714,389 | A | 2/1998 | Charlton et al. |
| 5,728,587 | A | 3/1998 | Kang et al. |
| 5,747,273 | A | 5/1998 | Khosravi et al. |
| 5,807,690 | A | 9/1998 | Sanders et al. |
| 5,877,029 | A | 3/1999 | Fuks et al. |
| 5,891,722 | A | 4/1999 | Fuks et al. |
| 5,968,758 | A | 10/1999 | Fuks et al. |
| 5,989,921 | A | 11/1999 | Charlton et al. |
| 6,020,147 | A | 2/2000 | Guire et al. |
| 6,348,323 | B1* | 2/2002 | Khosravi et al. ............... 435/7.9 |
| 6,485,982 | B1 | 11/2002 | Charlton |
| 2005/0136490 | A1* | 6/2005 | Rutanen ......................... 435/7.2 |

FOREIGN PATENT DOCUMENTS

| | | |
|---|---|---|
| EP | 0229359 | 7/1987 |
| EP | 316919 | 5/1989 |
| EP | 0362809 | 4/1990 |
| EP | 0281327 | 6/1993 |
| EP | 0560411 | 9/1993 |
| EP | 0565541 | 10/1993 |
| EP | 0280559 | 10/1995 |
| EP | 0299428 | 1/1996 |
| EP | 0565541 B1 | 12/1997 |
| JP | 2004528036 | 9/2004 |
| RU | 2110800 | 5/1998 |
| SU | 1614194 | 4/1988 |
| WO | WO8808534 | 11/1988 |
| WO | WO 99/46597 | 9/1999 |

OTHER PUBLICATIONS

Indian Examination Report dated Jul. 27, 2010 for Indian counterpart Application Serial No. 5175/DELNP/2007 filed Jul. 4, 2007.

Japanese Examination Report dated Feb. 2, 2010 for Japanese counterpart Application Serial No. 2004-528036 filed Aug. 12, 2003.

Boltovskaia, M.N. et al. Biull. Eksp. Biol. Med., (1991) 112(10): 397-400 (Russian), Boltovskaia, M.N. et al. Experimental Biology and Medicine (1992) 112(10): 1457-1460 (English).

Tkachenko & Petrunin. Vestn. Ross. Akad. Med. Nauk., (1995) 3: 40-44 (Abstract).

Actim Prom. 2004 Qualitative Test for Detection of Amniotic Fluid in the Vagina.

Nisson et al. 2004. Explorative Study of the Protein Composition of Amniotic Fluid by Liquid Chromatography Electrospray Ionization Fourier Transform Ion Cyclotron Resonance Mass Spectrometry. Journal of Proteome Research 3 (4):884-889.

Pekonen et al. 1989. Auf monoklonalen Antikörpern basierender immunoradiometrischer Assay für insulinähnliches, wachstumsfaktorbindendes Protein / Plazentaprotein 12 mit niedrigem Molekulargewicht (Übersetzung aus dem Englischen). Medix Biochemica. Minerva Institute for Medical Research.

Berggard et al. 1999. Histologic Distribution and Biochemical Properties of α1—Microglobulin in Human Placenta. American Journal of Reproductive Immunology 41:52-60.

Petrunin et al. 1977. Akusherstvo i Ginekologia 1:64-65.

Nasimova et al. 1993. Bulletin of Experimental Biology and Medicine 116(9):302-304.

Petrunin et al. 1990. regarding PAMG-1:369-77.

Briese et al. 1990. Exp. Clin. Endocrinol. 95(1):105-109.

Oy Medix Biochimica AB. 1988. Catalog. pp. 4-13.

Petrunin et al. 1980. Bulletin of Experimental Biology and Medicine 5:558.

Tatarinov, Y.S. et al. 1980. Two New Human Placenta-Specific α-Globulines: Identification, Purification, Characteristics, Cellular Localization and Clinical Investigation. Scrono Symposium No. 35:35-46, London and New York: Academic Press.

Petrunin et al. 1977. Akush Ginekol (Mosk) 62-4 (with an English Abstract).

Bohn, H. 1980. Protein Antigens of the Human Placenta. Proceedings of the Serno Symposia 35:23-34.

Cubbage, Michael L., et al. 1989. Structure of the Human Chromosomal Gene for the 25 Kilodalton Insulin-Like Growth Factor Binding Protein. Molecular Endocrinology 3:35:846-851.

Koninckx, P.R. et al. 1981. Prolactin Concentration in Vaginal Fluid: A New Method for Diagnosing Ruptured Membranes. British Journal of Obstetrics and Gynecology 88:607-610.

Petrunin, D.D. et al. 1988. A Comparative Study of Four Human Placental Proteins in the Course of Pregnancy. 50-52.

Seppälä, M. et al. 1994. Uterine endocrinology and paracrinotogy: insulin-like growth factor binding protein-1 and placental protein 14 revisited. Human Reproduction 9(5):917-925.

Bell, Stephen C. and John W. Keyte. 1988. N-Terminal Amino Acid Sequence of Human Pregnancy-Associated Endometrial $a_1$-Globulin, an Endometrial Insulin-like Growth Factor (IGF) Binding Protein—Evidence for Two Small Molecular Weight IGF Binding Proteins. Endocrinology 123(2):1202-4.

Bell, Stephen C. et al. 1991, Regulation of Insulin-Like Growth Factor-Binding Protein-1 Synthesis and Secretion by Progestin and Relaxin in Long Term Cultures of Human Endometrial Stromal Cells. Journal of Clinical Endocrinology and Metabolism 72(5):1014-1024.

Bischof, Paul. 1989. The Pregnancy Proteins (PP12. PP14 and PAPP-A): Their Biological and Clinical Relevance. American Journal of Perinatology 6(2):110-116.

Rutanen, E-M. et al. 1988. Monoclonal Antibodies to the 27-34K Insulin-like Growth Factor Binding Protein. Biochemical and Biophysical Research Communications 152(1):208-215.

Rutanen, E-M. et al. 1993. Measurement of insulin-like growth factor binding protein-1 in cervical/vaginal secretions: comparison with the ROM-check Membrane Immunoassay in the diagnosis of ruptured fetal membranes. Clinica Chimica Acta 214:73-81.

Rutanen, E-M, et al. 1996. Evaluation of a rapid strip test for insulin-like growth factor binding protein-1 in the diagnosis of ruptured fetal membranes. Clinica Chimica Acta 253:91-101.

Allander, S.V. et al. 1993. Gene Structures and Expressions. Growth Regulation 3(1):3-5.

Bell, Stephen C. et at, 1989. Monclonal Antibodies to Human Secretory Pregnancy-Associated Endometrial a1-Blobulin,' an Insulin-Like Growth Factor Binding Protein: Characterization and Use in Radioimmunoassay, Western Blots, and Immunohistochemistry. American Journal of reproductive Immunology 20:87-96.

Bohn, H. and W. Kraus. 1980. Isolation and Characterization of a New Placenta Specific Protein (PP12). Arch. Gynecol. 229:279-291.

Busby, W.H. Jr. et al. 1988. Purification of a 31,000-dalton insulin-like growth factor binding protein from human amniotic fluid. Isolation of two forms with different biologic actions. J. Biol. Chem. 263(28):14203-10.

Darj, Elisabeth and Sven Lyrenas. 1998. Insulin-like growth factor binding protein-1, a quick way to detect amniotic fluid. Acta. Obstet. Gynecol. Scand. 77:295-297.

Diamandi, Anastasia et al. 2000. Immunoassay of Insulin-Like Growth Factor-Binding Protein-3 (IGFBP-3): New means to Quantifying IGFBP-3 Proteolysis. Journal of Clinical Endocrinology and Metabolism 85(6):2327-2333.

Ehrenborg, Ewa at al. 1992. Congiguous Localization of the Genes Encoding Human Insulin-like Growth Factor Binding Proteins 1(IGBP1) and 3(IGBP3) on Chromosone 7. Genomics 12(3):497-502.

Hellemans, P. et al. 1992. Preliminary results with the use of the ROM-check immunoassay in the early detection of rupture of the amniotic membranes. European Journal of Obstetrics & Gynecology and Reproductive Biology 43:173-179.

Jeurgens-Borst, Anneke J.C.M et al. 2002. Use of insulin like growth factor binding protein-1 in the diagnosis of ruptured fetal membranes. European Journal of Obstetrics & Gynecology and Reproductive Biology 102:11-14.

Kim, He-Seong et al. 1997. Identification of a family of low-affinity insulin-like growth factor binding proteins (IGFBPs): Characterization of connective tissue growth factor as a member of the IGFBP superfamily. Proc. Natl. Acad. Sci. USA 94(24):12981-6.

Kishida, Tatsuro et al. 1996. Diagnosis of premature rupture of the membranes in preterm patients, using an improved AFP kit: comparison with ROM-check and/or nitrazine test. European Journal of Obstetrics & Gynecology and Reproductive Biology 69:77-82.

Koistinen, Riitta et al. 1986. Placental Protein 12 Is a Decidual Protein that Binds Somatomedin and Has an Identical NK-Terminal Amino Acid Sequence with Somatomedin-Binding Protein from Human Amniotic Fluid. Endocrinology 118(4):1375-1378.

Kubota, Takeyoshi and Hisaya Takeuchi. 1998. Evaluation of Insulin-Like Growth Factor Binding Protein-1 as a Diagnostic Tool for Rupture of the Membranes. J. Obstet. Gynaecol. Res. 24(6)411417.

Lockwood, Charles J. et al. 1994. Fetal membrane rupture is associated with the presence of insulin-like growth factor-binding protein-1 in vaginal secretions. Am. J. Obstet. Gynecol. 171(1):146-50.

Lockwood, Charles J. et al. 1991. Fetal Fibronectin in Cervical and Vaginal Secretions as a Predictor of Preterm Delivery. New England Journal of Medicine 325(1):669-674.

Luthman, Holger et al. 1989. Human insulin-like growth-factor-binding protein. Low-molecular-mass form: protein sequence and cDNA cloning. Eur. J. Biochem. 180:259-265.

Marinaro, Joe A. et al. O-glycosylation delays the clearance of human IGF-binding protein-6 from the circulation. European Journal of Endocrinology 142:512-516.

Ooi, Guck T. et al. 1990. Recognition of insulin-like-growth-factor-binding proteins in serum and amniotic fluid by an antiserum against a low-molecular-mass insulin-like-growth-factor-inhibitor/binding protein, Biochem. J. 267:615-620.

Povoa, Guilherme. 1984. Cross-reaction of serum somatomedin-binding protein in a radioimmunoassay developed for somatomedin-binding protein isolated from human amniotic fluid. Acta Endocrinologica 107:563-570.

Ragosch, V. et al. 1996. Insulin like growth factor binding protein 1 (IGFBP-1). Geburtsh. U. Frauenheililk. 56:291-296.

Rosenfeld, Ron. G. et al. 1999. The Insulin-like Growth Factor Binding Protein Superfamily: New Perspectives. Pediatrics 104:1018-1021.

Rutanen, Eeva-Marla and Fredrika Pekonen. 1991. Diagnosis of Premature Rupture of Fetal Membranes by the Measurement of Insulin-like Growth Factor Binding Protein-1 in Cervical Secretion. Am. J. Obst. Syn. 164(1) Abstract 38:258.

Seppala, Markku et al. 1983. Immunologic and Biological Properties and Clinical Significance of Placental Proteins PP5 and PP12. Annals New York Academy of Sciences 417:368-382.

Woltmann, Wiebke et al, 1995. Detection of Ruptured Fetal Membranes using Insulin-like Growth Factor-binding Protein-1. Z. Geburtsh. Neonatol. 199:243-244.

Zaraysky, E.I, et al. 1989. Immunoenzyme Assay of Placenta Specific $_{a1}$-Microglobulin in Donor Blood Serum. Voprosy Med. Khemii 5:130-132.

Rochelson, Burton L. et al. 1987. A Rapid Colorimetric AFP Monoclonal Antibody Tet for the Diagnosis of Preterm Rupture of the Membranes. Obstetrics & Gynecology 69(2):163-163.

Medix Biochemica. 2006. Actim PROM (product information).

Ballard, F.J. et al. 1990. Report on the Nomenclature of the IGF Binding Proteins. Journal of Clinical Endocrinology and Metabolism 70(3):817.

Berggard, Tord. 1998. Structure and distribution of alpha-1-microglobulin proteins. Lund University Doctoral Dissertation (abstract).

Lee, Yao-Lire et al. "Insulin-Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF-I and IGF-II Receptors." Molecular Endocrinology, 1988, pp. 404-411, vol. 2, No. 5.

Rutanen, Eeva-Marja et al. Radioimmunoassay of Placental Protein 12: Levels in Amniotic Fluid, Cord Blood, and Serum of Healthy Adults, Pregnant Women, and Patients with Trophoblastic Disease.' Am. J. Obstet Gynecol., Oct. 15, 1982, pp. 460-463, vol. 144, No. 4.

Rochelson. Burton L. et al. "Rapid Assay—Possible Application in the Diagnosis of Premature Rupture of the Membranes." Obstetrics & Gynecology, Oct. 1983, pp. 414418, vol. 62, No. 4.

Pekonen, Fredrika et al. "A Monoclonal Antibody-Based immunoradlometrlc Assay for Low Molecular Weight Insulin-Like Growth Factor Binding Protein/Placental Protein 12." Journal of Immunoassay, 1989, pp. 325-337.

Voller, Alister, Maggio, Edward T. (ed.). "Heterogeneous Enzyme-Immunoassays and Their Applications." Enzyme-Immunoassay, © 1980 CRC Press, Inc., pp. 181-196 (Chapter 9).

Bohn, H. et al. "New Soluble Placental Tissue Proteins: Their Isolation, Characterization,.Localization and Quantification " Immunology of Human Placental Proteins, 1982, pp. 67-81, supplement 4.

Rutanen, Eeva-Marja et al. "Synthesis of Placental Protein 12 by Human Decidua." Endocrinology, 1985, p. 1304-1309, vol. 116, No. 4.

\* cited by examiner

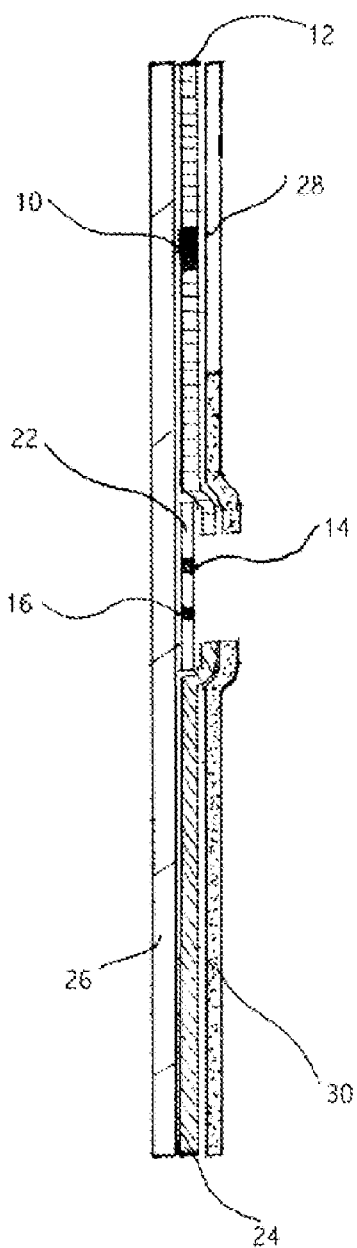
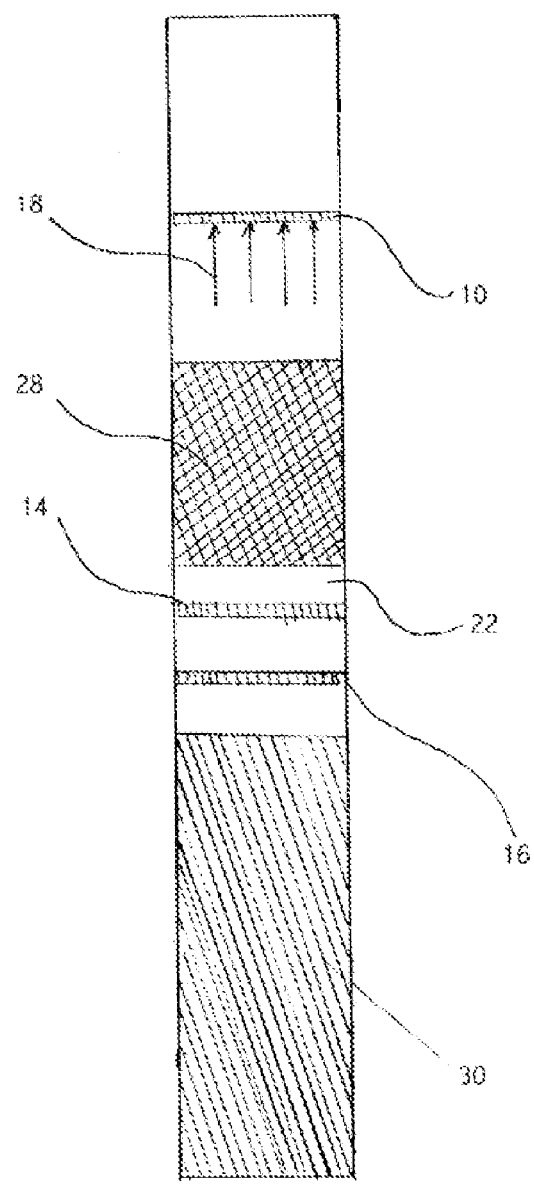
Fig. 1
Fig. 2

US 8,114,610 B2

DEVICES AND METHODS FOR DETECTING AMNIOTIC FLUID IN VAGINAL SECRETIONS

CROSS REFERENCE TO RELATED APPLICATIONS

This application is a continuation of U.S. patent application Ser. No. 10/524,668, filed on Mar. 8, 2006 which is a U.S. national phase application under 35 U.S.C. §371 of International Patent Application No. PCT/US2003/025125, filed Aug. 12, 2003, and claims benefit of U.S. Provisional Application No. 60/403,407, filed Aug. 13, 2002; all of which are incorporated by reference herein in their entireties. The International Application was published in English on Feb. 19, 2004 as WO 2004/014220 A1 under PCT Article 21(2).

FIELD OF THE INVENTION

The present invention relates to a diagnostic method for the accurate detecting of small quantities of amniotic fluid in vagina. In particular, the invention relates to using specifically selected monoclonal antibodies that specifically bind placental $\alpha_1$-microglobulin. More specifically, the present invention relates to the selection of a pair of anti-PAMG-1 antibodies ("basic pair") providing sensitivity sufficient for the detection of the minimum background concentration of PAMG-1 in the vaginal secretion of pregnant women. Further, the present invention relates to a solid phase immunoassay system comprising PAMG-1 antibodies, in which a combination of two or more anti-PAMG-1 antibodies are immobilized on the solid phase support of the device to precisely set up a predefined threshold level of sensitivity.

BACKGROUND OF THE INVENTION

Premature rupture of the fetal membrane (amniotic sac) occurs in about 10% of pregnant women and when not treated promptly, it is the cause of about 10% of all perinatal deaths. The term PROM (premature rupture of the fetal membranes) relates to the spontaneous rupture of the membranes 24 or more hours before the onset of labor either at term or preterm. PPROM refers to preterm premature rupture of membranes. Approximately about 30-50% of such premature ruptures occur before the 37th week of pregnancy. In such cases, definitive diagnosis of the rupture is extremely important since PROM is associated with a significant increase in the risk of an intrauterine infection and disturbance of development of the fetal lung system. Intrauterine penetration of such infections increases both maternal and perinatal morbidity and mortality by about ten percent. Immediate diagnosis of a rupture at 38 to 40 weeks of pregnancy is crucial, since once PROM is detected delivery should be induced as soon as possible. The rupture diagnosis is also important before 37 weeks of pregnancy because it enables prevention of intra-amnion infection and the stimulation of fetal lung development.

There is no "gold standard" available for the diagnosis of membrane rupture. PROM is a dynamic entity, so the interval between membrane rupture and implementation of the diagnostic modality, the presence of "high" leaks, intermittent leakage, variations in the incidence of PROM relative to populations, and consideration of material that has the capability of interfering with test results are factors that when not addressed result in inaccurate reporting. These inaccuracies may lead to errors in interpreting studies which aim to reveal the best tool for the identification of PROM.

The diagnosis of PROM has traditionally relied on the patient's report of fluid discharge from the vagina. Physical examination has the capability to diagnose unequivocally; however, there are times when the findings at examination are internally inconsistent or equivocal. This situation mandates the need for confirmatory diagnostic tests (Lockwood C. J. et al., Am. J. Obstet. Gynecol., 1994, v. 171, No 1, pp. 146-150). Several methods, all of them insufficient, are presently used to detect amniotic fluid in the vagina, such as the fern test (M. L. Friedman and T. W. McElin, "Diagnosis of Ruptured Fetal Membranes", *American Journal of Obstetrics and Gynecology* 1969, Vol. 100, pp. 544-550). This method is based on the detection of the amniotic fluid by the observation of so-called arborization when the amniotic fluid dries on a slide. This method, however, is not sufficiently accurate since it is based on the highly volatile properties of amniotic fluid in the vagina. It may produce false results in as many as 30 percent of the cases.

It has been also proposed to detect the rupture of the fetal membrane by employing several dyes: nile blue, acridine orange, bromthymol blue, nitrazine, etc. (M. L. Friedman and T. W. McElin, supra). This approach is inconvenient and has disadvantages related to the volatility of the chemical properties of amniotic fluid in the vagina and some possible admixtures to it. For instance, a vaginal infection can influence the results of the above tests. An early study of currently prevalent Nitrazine and Ferning tests indicated that these tests had high inaccuracy rates, which increased progressively when more than one hour has elapsed since membrane rupture, and became inconclusive after 24 hours. The study concludes that in cases of prolonged PROM these tests provide no better diagnostic information than that obtained by simple clinical evaluation (Gorodeski I. G, Haimovitz L., Bahari C. M., *Journal Perinat. Med,* 1982, v. 10, No 6, pp. 286-292). More recent data (Trovo S. et al., *Minerva Ginecol.* 1998, v. 50, No 12, pp. 519-512) on the tests are:

Nitrazine test shows sensitivity 70%, specificity 97%, accuracy 90%;

Ferning test shows sensitivity 70%, accuracy 93%.

It has been proposed recently to detect the rupture of fetal membranes based on an immunochemical analysis of the proteins in the amniotic fluid. Docked immunochemical analysis utilizes the following proteins of the amniotic fluid to detect a membrane rupture: alpha-fetoprotein, prolactin, fibronectin, and insulin-like growth-factor binding protein 1, see B. L. Rochelson et al, "Rapid Assay—Possible Application in the Diagnosis of Premature Rupture of the Membranes", in *Obstetrics and Gynecology,* 1983, v. 62, pp. 414-418; P. R. Koninckx et al., "Prolactin Concentration in Vaginal Fluid: a New Method for Diagnosing Ruptured Membranes", *British J. Obstetr. Gynecol.,* 1981, v. 88, pp. 607-610; P. Hellemans, et al., "Preliminary Results with the Use of the ROM Check Immunoassay in the Early Detection of Rupture of the Amniotic Membranes", *Eur. J. Obstet. Gynecol. Reprod. Biol.,* 1992, v. 43(3), pp. 173-179; Rutanen, E. M., et al., "Measurement of Insulin-like Growth-Factor binding Protein-1 in Cervical/Vaginal Secretions: Comparison with the ROM Check Membrane Immunoassay in the Diagnosis of Ruptured Fetal Membranes", *Clin. Chim. Acta.,* 1993, v. 214, pp. 73-81. Rutanen, E. M., et al. developed later a chromatographic test using the upside-down-positioned chromatographic membrane (FI-84863; U.S. Pat. No. 5,554, 504).

The methods which are based on the detection of alpha-fetoprotein (AFP) and prolactin (PRL) are unreliable since the blood/amniotic fluid ratio of AFP and PRL proteins is prone to significant variations. AFP and PRL are present in amniotic fluid in high concentrations during the second trimester of pregnancy only. The amniotic/serum protein concentration ratio for both proteins is only about 3 to 4 at term.

Another method based on the detection of fetal fibronectin in the vaginal secretions has also been found unsatisfactory. For instance, the presence of fetal fibronectin can take place even in the absence of the fetal membrane rupture (P. Hellemans, at al., "Preliminary Results with the Use of the ROM Check Immunoassay in the Early Detection of Rupture of the Amniotic Membranes", *Eur. J. Obstetr. Gynecol. Reprod. Biol.* 1992, v. 43(3), pp. 173-179; C. Lockwood, et al., "Fetal Fibronectin in Cervical and Vaginal Secretions as a Predictor of Preterm Delivery", *New England Journal of Medicine,* 1991, v. 325, pp. 669-674), thereby producing false-positive results.

All of these methods of detecting fetal membrane rupture, based on detection of alpha-fetoprotein, prolactin, and fibronectin, are inaccurate due to variable factors in control of the concentration of these proteins in amniotic fluid and of the relative concentration of these proteins in the amniotic fluid to that in blood serum.

As for the IGFBP-1 test update, there are contradictory data concerning its specificity and accuracy. A rapid strip test (PROM test by OY Medix Biochemica, Finland, also named Amni-check, MAST Diagnostica, Germany), has been developed for detecting the presence of IGFBP-1 in the vaginal secretions (Rutanen E M, Karkkainen T H, Lehtovirta J., Uotila J T, Hinkula M K, Hartikainen A L. "Evaluation of a rapid strip test for insulin-like growth factor binding protein-1 in the diagnosis of ruptured fetal membranes", *Clin Chim Acta* 1996 Sep. 30; v. 253(1-2), pp. 91-101). E. Rutanen reported that the detection limit of the test was set so that IGFBP-1 concentrations below 400 ng/ml in cervical secretion (below the 95$^{th}$ percentile of serum IGFBP-1 levels in pregnant women) should remain negative. However, in cases with bleeding, the test result should be interpreted with caution as blood straight from the placental bed may contain higher amounts of IGFBP-1 than blood from the cervical blood vessels.

All samples (n=55) in women with clinically confirmed PROM showed a positive result and 71 of 75 samples taken from asymptomatic women were negative according to the test. Among this set of samples, the test had sensitivity of 100% and specificity of 94.7%. This fact can be explained by insufficient specificity (cross reactivity) of the monoclonal antibody used at the first step of testing.

Among the 181 patients evaluated for suspected, but upon initial examination equivocal PROM, the test was positive in 64 cases and negative in 117 cases. Fifty of 64 positive patients (78.1%) delivered before 37 weeks of gestation, 42 (65.6%) within 2 weeks after sampling. Five of 117 patients with a negative test result had elective cesarean section for reasons unrelated to PROM. Among the other 112 patients, 102 (91.1%) delivered at term and 10 (8.9%) delivered before 37 weeks, seven of those (6.3%) within two weeks after sampling (E. Rutanen et al. 1996). Unfortunately, there is no data regarding sensitivity and specificity of the PROM test in women with unequivocal diagnosis of PROM.

In a study by W. Woltmann, Amni-check was used to detect IGFBP-1 in 150 amniotic fluid specimens and 50 vaginal secretion samples from women with clinically unconfirmed PROM. The test had a sensitivity of 97% and a specificity of 100% (Woltmann W. et al., *Z. Gebursh. Neonatal,* 1995, v. 199, pp. 243-244).

V. Ragosh evaluated diagnostic accuracy of the Amni-check test in the 75 vaginal secretion samples. The test showed a sensitivity of 100% and a specificity of 83%. Investigators reported that the false positive rate was strongly dependent on the labor activity. In women with uterine contractions, the test had a specificity of 59% (Ragosch, V. et al., *Geburish. U. Frauenheililk.,* 1996, Vol. 56, pp. 291-296).

In a study by E. Darj and S. Lyrenas (*Acta Obstet. Gynecol. Scand.,* 1998, v. 77, pp. 295-297), PROM-test had a sensitivity of 95.7% and a specificity of 93.1% among the patients with clinically confirmed diagnosis (women with obvious rupture of membranes or women with intact membranes). However, the sensitivity and specificity of PROM-test were only 70.8% and 88.2% respectively in the patients with suspected PROM. This discrepancy could be explained by the cut-off limit of the test (400 ng/ml), which makes it impossible to detect a small amount of amniotic fluid in vaginal secretions of patients with equivocal diagnosis (for instance, in the case of a small rupture).

Thus a significant background level of vaginal IGFBP-1 in women with intact membranes and a high cutoff threshold of the test may harm its sensitivity and specificity and thus impact the test's accuracy in patients with equivocal diagnosis. The admixtures of blood serum and/or inflammatory exudate could also impact the accuracy of test (see data of E. Darj et S. Lyrenas, above). The author of this test did not study the issue.

In attempting to avoid some of the above-mentioned drawbacks, two monoclonal antibodies were used against two binding sites for insulin-like growth factors to detect the unbound fraction of placental $\alpha_1$-microglobulin (U.S. Pat. Nos. 5,968,758; 5,597,700; 5,891,722; 5,877,029).

In these patents the identity of the two proteins, unbound PAMG-1 and IGFBP-1, was baselessly assumed. As a matter of fact, such assumption could be based only on the comparison of the primary structure and genes of these proteins.

In the above-mentioned patents it was not possible to set up the threshold of sensitivity of such test so as to achieve the highest degree of accuracy possible (99% or above). The common problem for such tests is background level and variability of background concentration of the detected substance. For instance, the background level of another protein, IGFBP-1, in the vaginal secretion of pregnant women, varies in a broad range from 0.5 to 90 ng/ml (see Rutanen's studies). The second important point is the possibility of admixtures of inflammation exudates or blood serum containing detected substance in vaginal secretion. This can cause false positive results.

Protein PAMG-1 was first described by D. Petrunin (Petrunin D. et al, *Akusherstvo i Ginekologia,* 1977, No. 1, p. 64, in Russian; see also PMID:65924 (PubMed-indexed for MEDLINE: "Immunochemical identification of organ specific human placental alpha-globulin and its concentration in amniotic fluid", *Akushersivo i Ginekologia* (Moscow) 1977 January, Vol. 1, p. 64)). Antibodies were obtained against the purified and isolated protein, and immunochemical methods permitted measuring the contents of the protein in amniotic fluid (including amniotic fluid taken from the vagina) at different stages of pregnancy. The concentration of the protein in blood and different organs of the fetus and adult was also measured.

This research group continued to publish new results on the protein during subsequent years, until 1990 (Petrunin, D. et al, "Comparative Study of Four Placental Protein During Gestation", *Akushersivo i Ginekologia,* 1988, No. 1, pp. 50-52; Zaraisky, E. et al, *Voprosy Med. Khemii,* 1989, No 5, pp. 131-132; Tatarinov, Y. et al, *Uspekhi Sovr. Biologii* 1990, Vol. 109, pp. 369-373; Boltovskaya, M. et al, *Bulletin of Experimental Biology and Medicine,* 1991, No. 7, pp. 397-400; Nasimova, S. V. et al, *Bulletin of Experimental Biology*

*and Medicine,* 1993 September, Vol. 116, No. 9, pp. 302-304 (all these papers are in Russian with English abstracts). D. Petrunin obtained the Invention Certificate on the method of isolation of PAMG-1 (#SU-1614184 A1, Priority year 1988).

In 1988-89 a few papers were published detailing the partial and full sequence of similar proteins, the Insulin-like Growth Factor Binding Proteins (IGFBP), obtained from the amniotic fluid, from placenta and from human hepatoma (Bell Set al, 1988; Luthman H. et al, 1989; Julkunen et al, 1988; Lee, Y. et al, 1988). The gene was localized in the piece 7p14-7p12 of the $7^{th}$ human chromosome. Before 1991, researchers used different names for this protein: $\alpha_1$-PEG, PP-12, IGFBP, BP-25, etc.

In 1980-82, Bohn isolated a protein from the placenta and called it PP-12. In his paper, he compared PP-12 to the PAMG-1 protein, discovered earlier, and discussed the similarities and differences between them.

In contrast to the other research publications was a paper by Bell et al (1988), who found polymorphism in the N-end peptide of the $\alpha_1$-PEG protein, namely in the in the $11^{th}$ and $12^{th}$ positions, and came to the conclusion that there were, in actuality, two different proteins rather than one.

S. Bell once again references his own paper regarding the two different proteins $\alpha_1$-PEG in amniotic fluid. This paper accepts the decision of the Nomenclature Committee of 1990 (Report on the Nomenclature of the IGF Binding Proteins, *Journ. Clin. Endocr. And Metabol.* 1990, 70, #3, p. 817), which decided that proteins AFBP, PP-12, $\alpha_1$-PEG, GH-Protein, Binding Proteins 28,26,25, JB-1 are identical and gave them all a general name hIGFBP-1.

A so-called free PAMG-1 was used to detect the fetal membrane rupture. However, as mentioned above, a test with high accuracy (>99%) was not created. This goal was achieved later with our new method and device, described in this Application. The present invention employs a method of selection of a pair of monoclonal antibodies to provide sensitivity sufficient to detect a very low concentration of PAMG-1 in the vaginal secretion, and also involves selection of some other anti-PAMG-1 antibodies, which in combination with the two antibodies mentioned above, allowed to precisely set up a predefined threshold of sensitivity for the strip device. This, in turn, made it possible to minimize the frequency of false positive results of the test.

The present invention started from the pioneer study D. Petrunin, who separated and described placental-alpha-microglobulin and carried out a thorough measurement of its concentration in the amniotic fluid, blood and some tissues using immunochemical methods. This publication is the public domain that should be taken into account by any researcher. The method of separation of PAMG-1 has been protected by an official author's certificate (#SU-1614184 A 1, Priority year 1988), an equivalent of a patent in the former USSR.

SUMMARY OF THE INVENTION

The present invention relates to the method for detecting a small quantity of amniotic fluid in vaginal secretions during pregnancy.

The present invention relates to the method for detecting PAMG-1 above the minimal background concentration of amniotic protein PAMG-1 in the vaginal secretion of pregnant women, which indicates the presence of amniotic fluid.

In a specific embodiment, the method for the detection of the PAMG-1 protein utilizes a pair of monoclonal antibodies specially selected to detect the minimum background concentration of PAMG-1 protein in vaginal secretion. This pair of antibodies has been used in combination with at least one additional anti-PAMG monoclonal antibody in order to precisely set up a given threshold of sensitivity of the test.

The invention further contemplates use of a combination of PAMG-1-capturing antibodies in one strip device to enable a more precise set up of the threshold of sensitivity in the method for detection of the amniotic protein PAMG-1 in the vaginal secretion. This approach provides greater control of sensitivity and dynamic range than use of a selected pair of antibodies alone.

The most appropriate sensitivity threshold level of the method is found to be close to 5 ng/ml since the upper level of PAMG-1 in vaginal secretion, which may be caused by inflammation, does not exceed 3 ng/ml, and on the other hand, the regular background level of PAMG-1 in vaginal secretion of healthy pregnant women is around 0.2 ng/ml. The significant gap between background level and threshold concentration of the detected substance minimizes false negative and false positive results. In an embodiment, the first step of recognizing of amniotic PAMG-1 takes place in the pad part of the strip device, where the specially selected and labeled antibody is located. The second step of the reaction takes place at the test region of dipstick device where the second antibody of the selected pair and preferably at least one additional anti-PAMG-1, antibody are immobilized.

In summation, we describe the method and device for detecting small quantities of amniotic fluid in the vagina of a pregnant woman. The method is preferably based on selection of the pair of monoclonal antibodies against placental $\alpha_1$-microglobulin (PAMG-1). The goal of selection was, first, to measure a minimum background concentration of PAMG-1 in the vaginal secretion. Having this information, any analytical technique capable of detecting PAMG-1 above that threshold level can be employed to detect amniotic fluid in vaginal secretions. Based on this information, one can create a device based on the use of the same pair and additional antibodies so as to lower and accurately set up the threshold of sensitivity of the device and thereby minimize the likelihood of false negative and false positive results.

Various combinations of capturing antibodies and fragments thereof, or combinations of any other molecules are possible with the same properties as the properties specified herein.

In one embodiment of the present invention the method comprises the contact of a sample containing PAMG-1 protein and the monoclonal antibody, the first one of the selected pair, which selectively detects PAMG-1. It further comprises the antibody that forms the antibody-PAMG-1 complex, and the step of detection of the antibody-PAMG-one complex by another labeled monoclonal antibody of the pair. It finally comprises the quantitative measurement of the low minimum background of PAMG-1 in vaginal secretion of pregnant women who do not have rupture of amniotic membranes. This method is often used in ELISA class tests.

In yet another embodiment of the present invention, the device implements the contact of a sample containing PAMG-1 protein and a labeled monoclonal antibody, the first one of the selected pair, which selectively detects PAMG-1. It further comprises the antibody that forms an antibody-PAMG-1 complex, the lateral flow of this complex, and the step of detection of the antibody-PAMG-1 complex by another monoclonal antibody recognizing PAMG-1 whereby the sensitivity threshold of the device is set up around the range of 5-7 ng/ml using additional antibodies with a higher accuracy than the accuracy that can be attained using the pair of PAMG-1-recognizing monoclonal antibodies.

BRIEF DESCRIPTION OF THE DRAWINGS

FIG. 1 is a schematic longitudinal sectional view of a device of the invention which may be used to detect the presence of PAMG-1 in order to diagnose the rupture of a fetal membrane.

FIG. 2 is a planar view of the device of FIG. 1.

DETAILED DESCRIPTION OF THE INVENTION

This invention addresses the above-mentioned problems of accurately detecting amniotic fluid in vaginal secretions by detecting very low concentrations of placental $\alpha_1$-microglobulin in vaginal secretion. This approach proved advantageous due to a low background level (around 0.2 ng/ml in vaginal secretion of pregnant women) of PAMG-1 concentration. The crucial point of this invention was the selection of the monoclonal antibody to detect the protein at low concentration, which permits quantification of these values and in turn, enables any analytical technique to be used to detect the level of PAMG-1. The presence of PAMG-1 at low concentration in vaginal secretion could be expected since permeability of capillary wall for blood proteins depends on posttranslational modifications of proteins and their interaction with other molecules (Marinaro J. A. et al: O-glycosylation delays the clearance of human IGF-binding protein-6 from the circulation; Eur J Endocrinol 2000, May; 142(5): 512; Schneeberger E. E.: Proteins and vesicular transport in capillary endothelium; Fed Proc 1983 may 15; 42(8):2419-24; Minshall R D et al: Vesicle formation and trafficking in endothelial cells and regulation of endothelial barrier function; Histochem Cell Biol 2002 February; 117(2):105-12; Del Vecchio P J et al: Endothelial monolayer permeability to macromolecules; Fed Proc 1987 June; 46(8):251 1-5; Siflinger-Birnboim A et al:Selectivity of the endothelial monolayer: effects on increase permeability; Microvasc Res 1998 November; 36(3):216-27; Ghinea N, Milgrom E A new function for the LH/CG receptor: transcytosis of hormone across the endothelial barrier in target organs; Semin Reproduct Med 2001; 19(1):97-101). Among the PAMG-1 molecules, which underwent the posttranslational modifications, or established a non-covalent bond with another molecules, are those whose penetration into the vaginal secretion is minimal. The concentration of such molecules in the vaginal secretion should be low, unless there is a breach in the amniotic sack. Heterogeneity of PAMG-1 molecules could also be the result of alternative splicing. Bell et al. presented data regarding two close, but different, proteins $\alpha_1$-PEG in amniotic fluid. Alpha$_1$-PEG is close to PAMG-1. The low or high penetration of different molecules into vaginal secretion occurs due to the selective permeability of the capillary walls and selective secretory processes. A successful immunoassay required detecting the low background concentration of PAMG-1 molecules in vaginal secretion.

A pair of monoclonal antibodies capable of such detection was successfully selected. The exact characteristics of the detected PAMG-1 molecules appear unimportant for the purposes of this invention, with one exception: its low concentration in the vaginal secretion must be certain. This parameter is sufficient to set the sensitivity threshold at a low level, maintaining a significant gap between the threshold of the test and background level of PAMG-1 concentration in vaginal secretion. This choice of the optimum threshold allows for filtering out both the potential false negative and false positive results of the test.

In particular, monoclonal antibodies (MAb) to placental alpha-l-microglobulin were studied based on their reaction in the system MAb-PAMG-1-conjugate of another MAb of the present invention (Example 4, Table 6). The highest titer has been found using specifically the pair M271–M52. However, using the pair MAb271-MAb52 and routine ELISA technique, the applicants failed to detect any concentration of PAMG-1 in vaginal secretion. A high sensitivity ELISA technique was developed for the pair MAb271-MAb52 (Example 5, Table 7) and employed to measure low (picogram-range) concentrations of PAMG-1 in vaginal samples (Example 6, Table 8), and then in both cervical and vaginal secretions of pregnant women (Example 7, Table 9). In ELISA, the first layer was formed from high-specificity MAb M271. The horseradish peroxidase conjugate contained MAb M52, diluted in the buffer that did not contain any inhibiting agents.

From Example 7, Table 9 one can see that the concentration of PAMG-1 in cervical and vaginal secretions of pregnant women without complications in pregnancy ranged from 0.05 to 0.22 ng/ml. One can see from this data that normal concentration of PAMG-1 (8 cases) is localized around some stable level. The relative stability of PAMG-1 both in the vagina and in cervix may serve an indication of the stability of the parameters of the method and of the standardized way of collecting samples;

mean levels of the normal concentration of PAMG-1 in the cervical secretion is around 151 pg/ml, in the vaginal secretion it is around 110 pg/ml;

in the case of gestational pathology, non-related to blood vessel disturbances (anemia, delay in fetus development), also a near-normal level of PAMG-1 was observed;

blood admixture is accompanied by an increase in the concentration of

PAMG-1 in the cervix, which was observed at the level 290 pg/ml, in contrast to the normal concentration of 151 pg/ml;

PAMG-1 level increases in the presence of symptoms from pre-term labor and gestosis, which may be accustomed to the increased permeability of fetal membranes to proteins;

given a leakage of amniotic fluid, the PAMG-1 level sharply increases (by a factor of 10-50).

As shown in the examples below, a pair of monoclonal antibodies M271 and M52 was selected for further development of the method, device and test kit.

The present invention thus relates in particular to a selected pair of monoclonal antibodies having binding affinity for PAMG-1, biological compositions including antibodies having binding affinity for PAMG-1, kits for detecting PAMG-1 using the antibodies of the present invention, and cell lines for producing antibodies of the present invention. The present invention also relates to devices and methods for detecting PAMG-1, as well as fetal membrane rupture, based on the presence of amniotic fluid in the vagina, as indicated by the presence of PAMG-1 in the vaginal secretion.

As will be described herein in greater detail, the present invention arises in part from a study with a pair of monoclonal antibodies that allow the detection of the minimum background concentration of PAMG-1 in the vaginal secretion of pregnant women. The minimum background concentration of PAMG-1 in vaginal secretion and its high concentration in amniotic fluid allows, first of all, to set up the threshold of sensitivity of a device at a low level and to thereby detect very small quantities of amniotic fluid in vaginal secretion, and secondly, to position the threshold of sensitivity of the device in an optimal way, specifically between the typical level of the low minimum background concentration of PAMG-1 in the vaginal secretion of pregnant women without rupture of fetal membranes, and a high typical level of PAMG-1 in the amniotic fluid. An additional monoclonal antibody or antibodies against PAMG-1 allows the more accurate set-up of the threshold of sensitivity of the device at a predefined level e.g., for semi-quantitative analysis. Further, because the presence of amniotic fluid in vaginal secretion is indicative of a fetal membrane rupture, the detection of PAMG-1 in vaginal secretion can also be used to detect fetal membrane rupture. All this in combination allows the minimizing of false results of the test detecting PROM and PPROM.

According to the present invention, antibodies specific for PAMG-1 can be incorporated into compositions of matter, kits, devices and methods used for the detection of PAMG-1 and thereby the occurrence of a fetal membrane rupture based on the presence of PAMG-1 in the vaginal secretion.

Protein PAMG-1

PAMG-1 is a protein that is present in the serum, amniotic fluid and vaginal secretion of pregnant women and in the serum of all people. PAMG-1 is present in the serum of non pregnant (0-60 ng/ml) and pregnant (5-120 ng/ml) women where the measured concentration depends on the pair of monoclonal antibodies that has been used for its detection (Example 1, tables 1, 2). It is known that the use of different pairs of antibodies against the same protein can yield a different measured concentration of that protein. Thus, in an analogous study by Diamandi A. et al (see Diamandi A. et al "Immunoassay of the Insulin-Like Growth Factor-Binding Protein-3" in *Journal of Clinical Endocrinology and Metabolism*, 2000, June, Vol. 85, No 6, pp. 2327-2333), three variants of ELISA showed three different concentrations of IGFBP-3, which Diamandi A. et al attributed to the ability of each antibody pair to pick a specific posttranslational modification of the protein molecules. PAMG-1 is found in amniotic fluid in a significantly higher concentration than in serum (2000-75000 ng/ml).

PAMG-1 was isolated in 1977 from amniotic fluid by D. Petrunin and was originally referred to as specific alpha-I globulin of placenta (D. Petrunin, et al., "Immunological Identification of Organ Specific alpha-1 Globulin of Human Placenta and Its Content in the Amniotic Fluid," in *Akusherstvo i Ginekologiya*, 1977, N 1, pp. 64-65, Moscow, USSR (see Example 2)).

A similar but not identical protein, identified as PP12 (placental protein 12), was later isolated and purified from placental and fetal membranes by Bohn, et al. ("Isolierung and Characterisierung eines Neuen Placentaspezifischen Proteins (PP12)," in *Arch. Gynecol.*, 980, Vol. 229, pp. 279-291). S. Bell, et al. reported the separation of endometrial PEG-1 protein, different from PP12 in two amino acid substituents (amino acids N11, 12) in the N-terminal peptides of 15 amino acids (S. Bell, et al., *American Journal of Reproductive Immunology*, 1989, Vol. 20, pp. 87-96).

In order to further characterize the proteins identified from amniotic fluid, a series of measurements were conducted for determining the molecular weight of PAMG-1. The immunoblotting method was used in order to determine the molecular weight of PAMG-1, which was found to be 32 kD (kilodalton, kD is an atomic mass unit) (Boltovskaya, M. N. et al., "Histochemical and Clinico-Diagnostic Study of the Placental Alpha-Microglobulin [PAMG-1] Using Monoclonal Antibodies," in *Bulletin of Experimental. Biology and Medicine*, 1991, No. 10, pp. 397-400). Applicants later assumed that PAMG-1 relates to the family of IGFBP proteins (see U.S. Pat. No. 5,968,758).

PAMG-1 can be present in different isoforms, i.e., having undergone different post-translational modifications. Antibodies may have differential specificity for one isoform over another, and this can be used to advantage in the assays of the invention.

Antibodies to PAMG-1

Originally, the monospecific antibodies to PAMG-1 were used (see, for example, Tatarinov, Y. et al, in *Uspekhi Sovr. Biologii,* 1990, Vol. 109, pp. 369-373). Later, antibodies were obtained capable of recognizing only those PAMG-1 molecules that were free of IGF-1 and 1GF-2 (U.S. Pat. No. 5,891,722).

Herein, the term "antibody" refers to any protein having a binding affinity as specified in this application, independent of the method used to obtain the protein. For example, the protein may be a monoclonal antibody or fragment thereof, or any molecule having a binding specificity as specified in this application.

According to the invention, PAMG-1 polypeptide separated from body fluids produced recombinantly or by chemical synthesis, and fragments or other derivatives or analogs thereof, including fusion proteins, may be used as an immunogen to generate antibodies that recognize the PAMG-1 polypeptide. Such antibodies include but are not limited to polyclonal, monospecific, monoclonal, chimeric, single chain, Fab fragments, and an Fab expression library. The anti-PAMG-1 antibodies of the invention may be cross reactive, e.g., they may recognize PAMG-1 from different species. Polyclonal antibodies have greater likelihood of cross reactivity. Alternatively, an antibody of the invention may be specific for a single form of PAMG-1. Preferably, such an antibody is specific for human PAMG-1.

Various procedures known in the art may be used for the production of polyclonal antibodies to PAMG-1 polypeptide or derivative or analog thereof. For the production of antibody, various host animals can be immunized by injection with the PAMG-1 polypeptide, or a derivative (e.g., fragment or fusion protein) thereof, including but not limited to rabbits, mice, rats, sheep, goats, etc. In one embodiment, the PAMG-1 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the PAMG-1 polypeptide, or fragment, analog, or derivative thereof, any technique that provides for the production of antibody molecules by continuous cell lines in culture may be used. These include but are not limited to the hybridoma technique originally developed by Kohler and Milstein (Nature 1975, 256:495-497), as well as the trioma technique, the human B-cell hybridoma technique (Kozbor et al., Immunology Today 1983, 4:72; Cote et al., Proc. Natl. Acad. Sci. U.S.A. 1983, 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 Dec. 1989). In fact, according to the invention, techniques developed for the production of "chimeric antibodies" (Morrison et al., J. Bacteriol. 1984, 159: 870; Neuberger et al., Nature 1984, 312:604-608; Takeda et al., 1985, Nature 314:452-454) by splicing the genes from a mouse antibody molecule specific for an PAMG-1 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476, 786 and 5,132,405 to Huston; U.S. Pat. Nos. 4,946,778) can be adapted to produce PAMG-1 polypeptide-specific single chain antibodies. Indeed, these genes can be delivered for expression in vivo. An additional embodiment of the invention utilizes the techniques described for the construction of Fab expression libraries (Huse et al., Science 1989, 246: 1275-1281) to allow rapid and easy identification of monoclonal Fab fragments with the desired specificity for an PAMG-1 polypeptide, or its derivatives, or analogs.

Antibody fragments that contain the idiotype of the antibody molecule can be generated by known techniques. For example, such fragments include but are not limited to: the F(ab)2 fragment which can be produced by pepsin digestion of the antibody molecule; the Fab fragments which can be generated by reducing the disulfide bridges of the F(ab)2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an PAMG-1 polypeptide, one may assay generated hybridomas for a product which binds to an PAMG-1 polypeptide fragment containing such epitope. For selection of an antibody specific to an PAMG-1 polypeptide from a particular species of animal, one can select on the basis of positive binding with PAMG-1 polypeptide expressed by or isolated from cells of that species of animal.

Specific Antibodies According to the Present Invention

Hybridoma cell lines according to the present invention are produced by the following procedure. First, mice having spleen and lymph node B-cells are immunized with PAMG-1. Hybridomas are then produced to immortalize the B-cells. The B-cells may be spleen and/or lymph node B-cells. Those hybridomas, which produce a monoclonal antibody having a binding affinity for PAMG-1, are then identified in an ELISA: first layer: PAMG-1; second layer: hybridoma supernatant; and third layer: conjugate of rabbit anti-mouse antibodies labeled by horse radish peroxidase. These identified hybridomas are then cultivated in vitro or in ascites and the monoclonal antibodies they produce are isolated. In a specific embodiment, the antibodies are from hybridomas N52, N271, and N42 as deposited with the Russian National Collection of Industrial Microorganisms Depository with accession nos. VKPM H-92, VKPM H-93 and VKPM H-94, respectively.

Compositions According to the Present Invention

The present invention is also directed to a series of compositions that include two or more antibodies according to the present invention. In one embodiment, the composition includes a pair of antibodies and a detectable marker attached to one of the pairs of antibodies. A variety of detectable markers may be used, including, but not limited to, stained particles, enzymes, fluorescent dyes, and radioactive isotopes. One particular example of a detectable marker is a gold stained particle having an average dimension in the range of 20 to 30 nm. Another example of a detectable marker is the horseradish peroxidase. For example, methods for attaching a detectable marker to an antibody are described in *Methods In Enzymology*, 1981, Vol. 73, pp. 3-46 by Harlow, E., and Lane, D.; in "Antibodies a Laboratory Manual," *Cold Spring Harbor Laboratory*, 1988, pp. 322, 323, and 343; and *Pierce Catalog*, pp. T9-T17 (1996). Suitable enzymes include, but are not limited to, alkaline phosphatase and horseradish peroxidase. Other markers or labels for use in the invention include colloidal gold, colored latex beads, magnetic beads, fluorescent labels (e.g., fluorescene isothiocyanate (FITC), phycoerythrin (PE), Texas red (TR), rhodamine, free or chelated lanthanide series salts, especially Eu3+, to name a few fluorophores), chemiluminescent molecules, radio-isotopes (125I, 32P, 35S, chelated Tc, etc.) or magnetic resonance imaging labels. Other markers include fluorescence quenching and fluorescence transfer markers, e.g., as used in homogenous as well as solid phase assays. Furthermore, in accordance with the invention a marker can be an epitope, binding partner, or "handle" for interaction with another molecule, such as biotin-streptavidin; glutathione-GST; hexahistidine-nickel; etc. The invention also contemplates using secondary antibodies, which are themselves detectably labeled, as markers (e.g., in a situation where the anti-PAMG-1 antibody pair uses antibodies with Fc portions from two different animal species).

In another embodiment, the composition may further include two or more monoclonal antibodies localized in the test region of the strip device of the invention.

Kits According to the Present Invention

The present invention also relates to kits for detecting PAMG-1. In one embodiment, the kit includes a pair of antibodies according to the present invention: one of them highly specific to PAMG-1. In one variation of the kit, one or another antibody includes a detectable marker attached to an antibody. In another variation, one or another antibody of a selected pair is attached to a solid support. In this variation, the mobilizable antibody of the selected pair includes a detectable marker. In another embodiment, the composition comprises three or more monoclonal antibodies, one of which is mobilizable and detectable, as this combination permits adjusting the threshold of sensitivity of an immunochromatographic assay.

In a specific embodiment, the highest binding affinity anti-PAMG-1 antibody is mobilizable and placed in the pad region of the device for initial sample contact. Another antibody is placed in the test region of the device. Alternatively, other monoclonal antibodies with high binding affinity for PAMG-1, albeit not as high as the highest binding affinity, can be prepared in different combinations to immobilize in the test region of the device to set up or tune a predefined threshold of sensitivity for the device of the invention. This can be done through routine experimentation, as shown in Example 11. Different compositions of antibodies establishes a threshold of signal detection for the device of the present invention at a predefined level.

Methods and Devices for Detecting PAMG-1

The present invention establishes that PAMG-1, particularly PAMG-1 present in amniotic fluid in much greater amounts than in normal vaginal fluid, is a useful analyte for detecting fetal membrane rupture that results in leakage of amniotic fluid into the vagina. In other words, it permits a diagnosis of premature rupture of membranes, i.e., the amniotic sac. The invention further establishes cut-offs for detecting PAMG-1 under normal conditions, various symptoms of vaginitis, and true membrane rupture. Having identified the analyte and the relative levels indicating membrane rupture, one of ordinary skill in the art can then employ, to full advantage, any analytical technique known for the detection of proteins to determine whether a condition of premature membrane rupture has occurred in a patient.

Immunoassays, particularly immunochromatographic assays, constitute a preferred technique in accordance with the invention, and immunoassays are set forth in detail below. These assays have the advantage of specificity, accuracy, speed, and economy.

The invention can also employ other methods for detecting and quantitating PAMG-1, although these methods may require expensive equipment and limit assays to laboratory setting. One such technique is mass spectrometry, e.g., using matrix-assisted laser-desorption (MALD1) time-of-flight (TOF) mass spectrometry (MS) with delayed extraction and a reflectron in the time-of-flight chamber. Preferably MALDI assays are performed on silicon arrays. An example of an array for MALDI is 200 μm circular gel pads at 350 μm centers, on oxidized silicon. A hydrophobic surface (repellent surface) between gelpads further provides a more focused matrix/protein spot for MALDI, thereby improving signal for quantitation. For example, spots produced using the Packard Bioscience system can be less than 200 μm in diameter. The Piezo system can deliver about 300 pL of MALDI matrix (e.g., DHB, sinapinic acid) to the exact position of the affinity capture agent-peptide spot to create a homogeneous peptide/matrix crystal. Desorption/Ionization (Karan, et al. Ion Processes, 1987, v. 78, pp. 53-68 or Zenobi, et al. Mass Spectrom. Rev. 1998, v. 17, pp. 337-366) from this crystal in a MALDI-MS (e.g., Perseptive Voyager) yields a mass spectrum where the height of a peptide peak is relative to the amount protein containing that peptide.

An alternative technique for use in the invention is capillary electrophoresis chromatography, which can permit quantitation of an analyte present in a small amount of sample.

Furthermore, quantitative biochemical techniques, such as polyacrylamide gel electrophoresis, high performance liquid chromatography, and the like may be employed, alone or in combination, to detect and quantitate the amount of PAMG-1 in a sample.

Immunological Methods and Devices for Detecting PAMG-1

Various means known in the art for detecting immunospecific binding of an antibody to an antigen can be used to detect the binding in accordance with the present invention. An early method of detecting interaction between an antigen and an antibody involved in analysis of the complex is by precipitation in gels. A further method of detecting an analyte-detector antibody binding pair includes the use of radioiodinated detector antibodies or a radioiodinated protein which is reactive with IgG, such as Protein A. These early methods are well known to persons skilled in the art, as reviewed in Methods in Enzymology, 1980, v. 70, pp. 166-198. By selecting an antibody and conditions that yield a positive result above the threshold values for PROM disclosed herein, one may employ this technology in the practice of the invention.

Later methods for determining the presence of an analyte in a sample using only one antibody included competitive binding assays. In this technique the antibody, which most often would be immobilized onto a solid support, would be exposed to a sample suspected of containing the analyte together with a known quantity of labeled analyte. The two analytes, the labeled analyte and the analyte in the sample would then compete for binding sites on the antibody. Either free labeled analyte or bound labeled analyte is determined and from this measurement the amount of competing analyte in the sample is known. A more complete description of this method is disclosed in "Basic Principles of Antigen-Antibody Reaction", Elvin A. Labat, (Methods in Enzymology, 70, 3-70, 1980). In this example the labeled analyte can be labeled with either a radioisotope or an enzyme label.

More current immunoassays utilize a double antibody method for detecting the presence of an analyte. These techniques are also reviewed in the above referenced volume of Methods in Enzymology. Therefore, according to one embodiment of the present invention, the presence of the individual markers are determined using a pair of antibodies for each of the markers to be detected. One of said pairs of antibodies is referred to herein as a "detector antibody" and the other of said pair of antibodies is referred to herein as a "capture antibody". One embodiment of the present invention thus uses the double antibody sandwich method for detecting PAMG-1 in a sample of vaginal fluid. In this method, the analyte is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Common early forms of solid supports include plates, tubes or beads of polystyrene, all of which are well known in the field of radioimmunoassay and enzyme immunoassay. More recently, a number of porous materials such as nylon, nitrocellulose, cellulose acetate, glass fibers and other porous polymers have been employed as solid supports.

Thus, in a specific embodiment, the device of the invention comprises means for conducting an immunochromatographic assay ("immunochromatographic assay device"). Such a device comprises a solid phase means for conducting a liquid. As used herein, the term "solid phase means for conducting a liquid" refers to a solid support that allows migration of a liquid therethrough, e.g., via capillary action. A typical product of this nature is a nitrocellulose membrane, which may be prepared by methods well known to those skilled in the art.

Many immunochromatographic assay means and formats are known in the art, and can be used in the practice of the present invention. Immunochromatographic assays using a membrane as a solid support in a dipstick or flow-through device are well established for use in the clinical laboratory and for alternative, i.e., non-laboratory, site testing. The usual presentation for an immunochromatographic assay device is a membrane (cellulosic or non-cellulosic) enclosed in a plastic holder. The plastic holder keeps the membrane in a suitable configuration in order to ensure correct functioning of the entire device. There are many variations of the basic structure of assay devices. For example, Litman et al. (U.S. Pat. Nos. 5,156,952 and 5,030,558) describe an assay method and device for determining the presence of a minimum amount of an analyte in a sample. Ullman et al. (U.S. Pat. Nos. 5,137,808 and 4,857,453) describe a device to house an assay membrane that includes self-contained liquid reagents to aid sample flow. Dafforn et al. (U.S. Pat. No. 4,981,768) describes a device with ports for applying sample and extra liquid. Corti et al. (European Patent Application No. 89118378.2), Greenquist et al. (U.S. Pat. No. 4,806,312) and Berger et al. (U.S. Pat. No. 5,114,673) also describe assay devices.

Preferably, the immunochromatographic assay means includes a control to indicate that the assay has proceeded correctly. The control can be a specific binding reactant at a spot more distal from the sample application point on the solid phase support than the detection zone that will bind to labeled reagent in the presence or absence of analyte, thus indicating that the mobilizable receptor has migrated a sufficient distance with the liquid sample to give a meaningful result.

Suitable labels for use in immunochromatographic assays include enzymes, fluorophores, chromophores, radioisotopes, dyes, colloidal gold, colloidal carbon, latex particles, and chemiluminescent agents. When a control marker is employed, the same or different labels may be used for the receptor and control marker.

One embodiment of the present invention uses a flow-through type immunoassay device. Valkirs et al. (U.S. Pat. No. 4,632,901) discloses a device comprising antibody, specific to an antigen analyte, bound to a porous membrane or filter to which is added a liquid sample. As the liquid flows through the membrane, target analytes bind to the antibody. The addition of the sample is followed by the addition of a labeled antibody. The visual detection of the labeled antibody provides an indication of the presence of the target analyte in the sample.

Another example of a flow-through device is disclosed by Kromer et al. (EP-A 0 229 359), which describes a reagent delivery system comprising a matrix saturated with a reagent or components thereof dispersed in a water soluble polymer for controlling the dissolution rate of the reagent for delivery to a reaction matrix positioned below the matrix.

In migration type assays, the solid phase support, e.g., membrane, is impregnated with the reagents needed to perform the assay. An analyte detection zone is provided in which labeled analyte is bound and the results of the assay are read. For example, see Tom et al. (U.S. Pat. No. 4,366,241), and Zuk (EP-A 0 143 574). Migration assay devices usually incorporate within them reagents that have been attached to colored labels such as colloidal gold or carbon, thereby permitting visible detection of the assay results without addition of further substances. See for example, Bernstein (U.S. Pat. No. 4,770,853), May et al. (WO 88/08534), and Ching et al. (EP-A 0 299 428). All of these known types of flow-through devices can be used according to the present invention.

Direct labels are one example of labels that can be used in immunochromatographic assays according to the present invention. A direct label has been defined as an entity, which in its natural state, is readily visible, either to the naked eye, or with the aid of an optical filter and/or applied stimulation, e.g. U.V. light, to promote fluorescence. Examples of colored labels that can be used according to the present invention, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionuclide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in Methods in Enzymology, 70. 419-439, 1980 and in U.S. Pat. No. 4,857,453.

In a specific embodiment, the diagnostic device of the present invention comprises a membrane assembly having a detection section proximal to the point of introduction of the sample, and a capture section downstream from that position. The detector section contains antibodies (detector antibodies), which will react with any analytes of the present invention that are present in the sample. The detector antibodies are reversibly immobilized onto the membrane and will migrate with the sample, when in use. It is preferred although not essential, that the detector antibodies are labeled, for example, with a radionuclide, an enzyme, a fluorescent moiety, luminescent moiety or a colored label such as those described in the prior art, and discussed above. Specifically, one could employ a reactive label, so that for example, the antibody would appear gold before capture of the antigen, and would change to purple upon capture.

The capture section which, as stated, is downstream from the detector section, comprises capture antibodies, which are irreversibly immobilized onto the solid support, each antibody immobilized at a different position in the capture section. The antibodies and necessary reagents are immobilized onto the solid support using standard art recognized techniques, as discussed in the flow-through type immunoassay devices discussed previously. In general, the antibodies absorbed onto the solid supports as a result of hydrophobic interactions between non-polar protein substructures and non-polar support matrix material.

A particular advantage of the immunochromatographic assay technology of the present invention is that it overcomes the inability of these assays to provide quantitative data. Thus, the capture section can contain a mixture of immobilized antibodies specific for PAMG-1, such that a signal is only produced when the amount of PAMG-1 in the sample exceeds the desired detection threshold.

In addition, the present invention contemplates use of homogeneous immunoassay formats. One example of such a competitive homogeneous method is found in U.S. Pat. No. 3,817,837 by Rubenstein and Ullman, which describes a technique in which ligand and enzyme-bound-ligand compete for antibody binding sites. Since binding of the antibody to the enzyme-bound-ligand alters its enzymatic activity, the concentration of ligand present can be estimated by measuring the rate at which such a mixture converts substrate to product. Thus, in a homogeneous method, the detectable property of the label is inherently different depending on whether bound or unbound. In its bound state, the label will have greater or lesser signal intensity. Usually, binding of antibody to the labeled ligand causes a decrease in signal intensity, e.g., when the label is an enzyme. Typical products in this category include the EMIT line of enzyme immunoassays from Syva Company and the TDX line of fluorescence polarization immunoassays from Abbott Diagnostics. A particular homogeneous assay could be prepared with the disposition of all of the analytes on beads, in which event the sample would be introduced and the beads thereafter spun down and detected.

Other examples of biological diagnostic devices that can be used according to the present invention include the devices described by G. Grenner, P. B. Diagnostics Systems, Inc., in U.S. Pat. Nos. 4,906,439 and 4,918,025. The Grenner '439 device comprises a diagnostic test element and a sample application unit comprising a fluid delivery element that is characterized as having a layer with a plurality of grooves for the delivery of the sample to the test element. Grenner '025 relates to a device that includes a sample introducing means such as a membrane adjacent to which is positioned a capillary containing a fixed reagent and a waste liquid reservoir. Release of the fixed reagent from the capillary completes the reaction after the sample is deposited, and excess liquid is retained by the waste reservoir, so that the device is self-contained.

While the measurement with a membrane is preferred, it is to be understood that other techniques and corresponding sensor devices may likewise be used in similar fashion to the above. There are currently available several types of automated assay apparatus, which can undertake an assay on a number of samples contemporaneously. These automated assay apparatuses include continuous/random access assay apparatus. Examples of such systems include OPUS™ of PB Diagnostic System, Inc. and the IMX™ Analyzer introduced by Abbott Laboratories of North Chicago, Ill. in 1988. In general, a sample of the test fluid is typically provided in a sample cup and all the process steps including pipetting of the sample into the assay test element, incubation and reading of the signal obtained are carried out automatically. The automated assay systems generally include a series of workstations each of which performs one of the steps in the test procedure. The assay element may be transported from one workstation to the next by various means such as a carousel or movable rack to enable the test steps to be accomplished sequentially. The assay elements may also include reservoirs for storing reagents, mixing fluids, diluting samples, etc. The assay elements also include an opening to permit administration of a predetermined amount of a sample fluid, and if necessary, any other required reagent to a porous member. The sample element may also include a window to allow a signal obtained as a result of the process steps, typically a fluorescent or a colorimetric change in the reagents present on the porous member to be read, such as by a means of a spectroscopy or fluorimeter, which are included within the assay system. The automated assay instruments of PB Diagnostic Systems, Inc. are described in U.S. Pat. Nos. 5,051,237; 5,138,868; 5,141,871 and 5,147,609.

Further classes of immunochemical analyzer systems, which can be used in practicing the present invention, are the biosensors or optical immunosensor systems. In general an optical biosensor is a device that uses optical principles quantitatively to convert chemical or biochemical concentrations or activities of interest into electrical signals. These systems can be grouped into four major categories: reflection techniques; surface plasmon resonance; fiber optic techniques and integrated optic devices. Reflection techniques include ellipsometry, multiple integral reflection spectroscopy, and fluorescent capillary fill devices. Fiber-optic techniques include evanescent field fluorescence, optical fiber capillary tube, and fiber optic fluorescence sensors. Integrated optic devices include planer evanescent field fluorescence, input grading coupler immunosensor, Mach-Zehnder interferometer, Hartman interferometer and difference interferometer sensors. Holographic detection of binding reactions is accomplished detecting the presence of a holographic image that is generated at a predetermined image location when one reactant of a binding pair binds to an immobilized second reactant of the binding pair (see U.S. Pat. No. 5,352,582, issued Oct. 4, 1994 to Lichtenwalter et al.). Examples of optical immunosensors are described in general in a review article by G. A. Robins (Advances in Biosensors), Vol. 1, pp. 229-256, 1991. More specific description of these devices are found for example in U.S. Pat. Nos. 4,810,658; 4,978,503; and 5,186,897; R. A. Brady et al. (Phil. Trans. R. Soc. Land. B 316, 143-160, 1987) and G. A. Robinson et al. (in Sensors and Actuators, Elsevier, 1992).

The methods and corresponding kits of the present invention are capable of incorporation and practice within a variety of optical measurement systems. Specifically, while the kits and materials of the present invention may be practiced in an immunoassay format, such format itself is capable of embodiment in a variety of optoelectronic detection systems. More particularly, a variety of optical immunosensor technologies are already known that may be facilitated and implemented in the practice of the present invention. Thus, for example, devices and techniques such as reflection techniques, surface plasmon resonance, fiber optic waveguide techniques and integrated optic devices, may all be adopted and specifically configured to detect and display the results of the examination of a patient's biological sample in accordance with the present method. Particular reflection techniques, such as reflectometry and ellipsometry, and the specific use of optical fibers, optical waveguides, fluorescent capillary fill devices and integrated optical biosensors, present but a few of the variant techniques and equipment that may be employed. A general review of these devices may be found in Robinson, G. A., Optical Immunosensors: An Overview, Advances in Biosensors, Vol. 1, pp. 229-256 (1991).

More particularly, ellipsometry relies on the direction of a polarized light beam first against a reference surface (a standard) and thereafter against the sample surface, following which a comparison of the nature and extent of the resulting reflections can be made. Particularly, the binding of analyte to receptor molecules will be measured as a chain the thickness of the surface relative to the reference surface.

In the instance of multiple internal reflection spectroscopy, for example, the ligand and its receptor may be covalently immobilized on the optical surface of a planar, fused-quartz waveguide after which a light beam may be internally reflected within the waveguide and would penetrate into a solution adjacent the waveguide, so that refractive differences would be capable of measurement as between the standard and the sample. In this particular format, a fluorescent label may be associated and measurements of fluorescence resultantly taken to determine the present extent of binding.

An additional technique utilizes the technology known as fluorescent capillary fill device. In this particular technology, two glass plates held apart by a gap of capillary dimension are utilized. Receptor molecules may be immobilized onto the base plate, which also acts as an optical waveguide. Competitive or sandwich assays utilizing FITC labeling may be performed and induced fluorescence is coupled into the waveguide with signal from bound as opposed to unbound sources. Such signal is discriminated by its angular divergence upon exiting the waveguide. Surface Plasmon Resonance (SPR) devices have also been prepared which operate in response to the coupling of light incident upon a thin metal film into surface modes associated with collective electron oscillations within the metal film. Resonance condition is dependent upon the optical characteristics of the metal film, its thickness, the refractive indices of the dielectric on either side of it, and the angle of incidence of light. Receptor molecules are bound to the top side of the metal film, and the light is directed at the bottom side of the film, such as through a prism substrate. The target analyte, when binding to these receptors, will cause a shift in the resonance condition because of the change it produces in the local refractive index. Resonance is observed by a monitoring of the reflected light intensity as the angle of incidence at the light beam on the metal film surface varies. The change in resonance angle will directly correlate with the amount of analyte bound.

The techniques involving fiber optic systems include the evanescent field fluorescence. In this instance, the cladding is removed from the end of an optical fiber, thus producing a sensor element that evanescently interacts with the surrounding medium. Receptor molecules are bound to the exposed fiber surface, and direct assays may be performed utilizing the natural fluorescence of the receptor and conjugate proteins. Competitive or sandwich assays may be performed using FITC labeling to achieve greater sensitivity. In operation, a light wave is coupled into the fiber, and a portion of the evanescently produced fluorescence is coupled back into the fiber and propagated back to a detector.

A further technique utilizing optical fiber technology involves the optical fiber capillary tube, in which a bare fiber optic is enclosed within a cylindrical fill chamber, producing a sensor element that interacts evanescently with the portion of the fill volume immediately surrounding the fiber. Receptor molecules may be bound to the exposed fiber surface and sandwich or competitive displacement assays may be performed. A light wave would be coupled into the fiber, and a portion of the evanescently induced fluorescence would be coupled back into the fiber and propagated back to a detector. The signal from the target analyte versus the background sources is discriminated by its angular divergence upon exiting the fiber. Other fiber optic techniques such as fiber optic fluorescence may be adapted to the present invention utilizing certain of the same principles enunciated above.

Further photonic techniques such as interferometry include the disposition of a thin-film waveguide having, for example, two paths, on the first of which receptor molecules may be immobilized while the second is shielded to provide a reference channel. Laser light, for example, may be coupled into the waveguide and split down the two paths, so that changes in the refractive index and thickness of the covering letter may be detected by the result of a phase shift in the beam, that will, in turn, correlate with the amount of analyte bound. A variation on this approach is identified in the Hartman interferometer, where a single path multimode thin film planar waveguide is prepared. Receptor molecules may be immobilized on this path, and light from a laser may be coupled into the waveguide so that two modes propagate down the path. The optics of multimode geometries are such that the higher order mode has a large evanescent field, providing a signal mechanism, and the lower order mode has practically no evanescent field, providing a reference mechanism. Binding with the target analyte will cause related changes in the refractive index and thickness of the covering layer over the path which will be detected by the evanescent field of the higher order mode, causing a phase shift in that mode. As the lower order or reference mode is blind to such changes, no phase shift will be experienced, and the measured difference between the signal and reference beams will be capable of correlation to determine the amount of analyte bound.

While the foregoing discussion has provided both in general terms and some detail, various techniques available in optical sensor technology are adaptable to the practice of the present invention. It is to be understood that the above recitation is by no means exhaustive or limitative, as a variety of extant technologies may be adopted, that will successfully measure differences in binding and, consequently, the presence and amount of the respective markers or analytes of interest herein. Of course, as emphasized above, no matter what technology is employed, the practice of the invention comprises simultaneous detection and measurement of at least three analytes.

Immunochromatographic Methods for Detecting PAMG-

Embodiments of the methods of detecting PAMG-1 according to the present invention are described below.

In one embodiment of the method, PAMG-1 is detected in a sample through the contact of a sample containing PAMG-1 with an immunoassay system according to the present invention to form an antibody-PAMG-1 complex. The antibody-PAMG-1 complex is then detected. In one variation of this embodiment, the antibody includes a detectable marker, the step of detecting the antibody-PAMG-1 complex, which includes the detectable marker.

In another embodiment of the method, PAMG-1 is detected in a sample by putting the sample in contact with an antibody which has a highly specific binding affinity for PAMG-1 (like M271, exemplified infra), thus forming the antibody M271-PAMG-1 complex. The complex then comes into contact with an immobilized second antibody (e.g., like M52). The second antibody is immunologically distinct from and not cross-reactive to the first antibody, so that such antibodies can simultaneously bind to the PAMG-1 molecule. The immobilized antibody binds to the mobile antibody PAMG-1 complex to form the immobilized antibody PAMG-1 antibody complex. PAMG-1 is detected by detecting this heterotrimer complex. As noted above, the antibody with high specificity for PAMG-1 is preferably used for the initial recognition of PAMG-1.

When the above-described method includes the use of one antibody of the selected pair labeled with a detectable marker, a variation of the method includes putting the sample in contact with the first, labeled antibody prior to contact of the sample with the second, immobilized antibody. In this variation, the labeled antibody serves to bind to PAMG-1 in the sample. Yet another embodiment of the method includes the following steps: adding a fluid sample containing PAMG-1 to a mobilizable, labeled antibody region of porous material which permits migration of antibodies and proteins therethrough, the antibody region including a mobilizable antibody which has a high specificity for PAMG-1 resulting in the attachment of the antibody to PAMG-1 to form an antibody PAMG-1 complex; migration of the complex to the test region containing a second antibody immobilized therein, which second antibody has a binding affinity for PAMG-1 resulting in the second antibody binding to the labeled antibody- PAMG-1 complex to form an immobilized complex; and detecting the immobilized complex in the test region.

Yet another embodiment of the method, is a standard sandwich assay, in which an unlabeled antibody is immobilized on any surface. Addition of fluid sample containing PAMG-1 results in binding of PAMG-1 by the immobilized antibody to form an antibody PAMG-1 complex. Addition of labeled antibody results in formation of an immobilized complex composed of immobilized antibody PAMG-1-labeled antibody and detection of this complex.

According to the above-described methods, the antibodies may include a detectable marker or label, the step of detecting the antibody-PAMG-1 or PAMG-1-antibody complex including detection of the detectable marker or label. Examples of detectable markers that can be used include stained particles, enzymes, dyes and radioactive isotopes. In a specific embodiment, the detectable marker is a stained particle of gold, e.g., having an average dimension between about 20 nm and 30 nm. In yet another embodiment, the detectable marker is horseradish peroxidase.

Exemplary Devices for Detecting PAMG-1

A variety of devices are envisioned for detecting protein PAMG-1 in a sample. A specific embodiment of the device of the present invention for detecting PAMG-1 is described in FIGS. 1-2. Devices according to the present invention preferably can detect PAMG-1 in a sample where the concentration of PAMG-1 is between about 5 ng/ml and 50 µg/ml. It is also preferred that the devices have a detection threshold of about 5-7 ng/ml. The wider the gap is between the background concentration of PAMG-1 and the threshold of sensitivity of the detecting device, the lower the likelihood of false positive results. In this section, different possible embodiments of devices according to the present invention, are embodied within the device illustrated in FIGS. 1, 2. It is noted that this device can be designed to simply detect the preence of PAMG-1 in a sample of vaginal secretion.

The term Aabout@ as used herein means within an acceptable error range for the particular value as determined by one of ordinary skill in the art, which will depend in part on how the value is measured or determined, i.e., the limitations of the measurement system. For example, Aabout@ can mean within I or more than 1 standard deviations, per the practice in the art. Alternatively, Aabout@ can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Description of a Device of a Present Invention

For purposes of exemplification, this description refers to monoclonal antibodies exemplified infra. However, it is not necessary that these specific monoclonals be used. As shown in FIGS. 1 and 2, the device comprises a strip-like body composed of several sequentially interconnected elements. More specifically, part 12 of the device comprises a pad, which contains M271 antibody region 10, in which the M271 antibodies are labeled, e.g., by stained particles SP (not shown in the drawings). Pad 12 may be made of a fiberglass tissue or any other material, which is porous and permits the migration of various particles and substances of a sample. Stained particles may comprise gold particles having an average dimension within the range of 20 to 30 nm. M271 antibody region also contains mouse IgG immunoglobulin labeled by the same stained particles. The labeled M271 antibodies and mouse IgG immunoglobulin are introduced into the band part 10 of pad 12 by impregnating pad 12 with a solution of labeled M271 antibodies and labeled mouse IgG. The solution of M271 antibodies and mouse IgG immunoglobulin may be introduced in nitrocellulose membrane 22 using drawing pen or microdrop forming device. Connected to one end of pad 12 in its longitudinal direction are [a] nitrocellulose membrane 22, which contains a test region 14 and a control region 16. Both the test region 14 and control region 16 are arranged transversely to the device over its entire width. Test region 14 is a band portion of nitrocellulose membrane 22. Test region 14 contains M52 antibodies attached to nitrocellulose membrane 22. Control region 16 contains anti-mouse anti immunoglobulin antibodies attached to nitrocellulose membrane 22. Control region 16 crosses the entire width of strip 22. A filter paper membrane 24 is connected to the end of nitrocellulose membrane 22, which is opposite to the end of nitrocellulose membrane 22 connected to pad 12. A filter paper membrane 24 is connected to the end of nitrocellulose strip 22 in its longitudinal direction. The surface of the device is coated with special protective films 28 and 30, e.g., thin adhesive tapes specially designed for strip devices. Arrows 18 are drawn on the surface of film 28 in order to show the sample application end of pad 12. Pad 12, nitrocellulose membrane 22 and filter paper strip 24 are attached to an adhesive rigid plastic base 26.

Captions to FIGS. 1, 2
10—M271 antibody region;
12—pad;
14—test region;
16—control region;
18—arrows;
22—nitrocellulose membrane;
24—filter paper membrane;
26—adhesive rigid plastic base;
28—partially transparent protective film with arrows;
30—non-transparent protective film.

Preferred Embodiment of the Device of the Present Invention

In the embodiment described in this section, the device includes an M271 antibody pad region 10 formed of a porous sample application matrix that permits migration of antibodies and proteins therethrough. The M271 antibody region 10 includes the M271 antibody, which is capable of highly specific binding to PAMG-1. Introduction of fluid sample containing PAMG-1 into M271 antibody region results in the attachment of the M271 antibody to PAMG-1 to form the antibody M271-PAMG-1 complex. The device also includes a test region 14 in fluid connection with M271 antibody region 10 formed of a porous material which permits migration of antibodies and proteins therethrough. Test region 14 includes the M52 antibody immobilized in test region 14 which is also capable of binding to PAMG-1. The M52 antibody is immunologically distinct from the M271 antibody such that the M271 and M52 antibodies can simultaneously bind to PAMG-1. Introduction of a fluid sample to the M271 antibody region 10 results in the migration of the antibody M271-PAMG-1 complex into the test region 14 where the antibody M271-PAMG-1 complex binds to the M52 antibody and is immobilized in the test region by the M52 antibody. The device detects PAMG-1 in a sample based on the presence of the M52 antibody immobilized in test region 14. According to this embodiment, both antibodies are antibodies according to the present invention. The procedure of selection of the pair of antibodies described above can be reproduced by any one experienced in the art. As a result, only PAMG-1 forms an antibody M271-PAMG-1-M52 antibody complex which is immobilized in the test region 14. Thus, the presence of the M52 antibody immobilized in the test region 14 is indicative of the presence of PAMG-1 in the sample.

In this embodiment of the device, the M271 antibody is attached to a detectable marker which is used to detect PAMG-1 immobilized in the test region 14. Examples of detectable markers that may be used include, but are not limited to, stained particles, enzymes, dyes, fluorescent dyes, and radioactive isotopes. In one embodiment, the detectable marker is gold particles having an average dimension between about 20-30 nm. In one embodiment, the M271 antibody is a labeled antibody in a freeze-dried state.

In a variation of the embodiment where the M271 antibody in the M271 antibody pad region is labeled with a detectable marker, the device further includes test region, which contains the M52 antibody. The pad region and test region are in fluid connection.

In yet another embodiment of the device, also embodied within the device illustrated in FIGS. 1-2, the device has a strip-like body with proximal and distal ends. The M271 antibody region 10 of the strip-like body is made of a material which permits the migration of antibodies and proteins therethrough. The M271 antibody region 10 of the strip-like body includes the M271 antibody, which has a highly specific binding affinity for PAMG-1, introduction to the M271 antibody pad region of a fluid sample containing PAMG-1, which results in the attachment of the M271 antibody to PAMG-1 to form the antibody M271-PAMG-1 complex.

The strip-like body also includes a test region 14, which is proximal to the M271 antibody region 10 and is in fluid connection with the M271 antibody region 10. The test region 14 is formed of a material which permits migration of antibodies and proteins therethrough. The test region 14 includes the M52 antibody immobilized in the test region 14, which has a binding affinity for PAMG-1, the introduction of the fluid sample to the M271 antibody region 10 resulting in the migration of the antibody M271-PAMG-1 complex to the test region 14 where the antibody M271-PAMG-1 complex binds to the M52 antibody and is immobilized in test region 14 by the M52 antibody. The test region also includes M42 antibody and M52 antibody immobilized in the test region 14. The non-labeled M52 and M42 antibodies in combination allow fine-tuning of the sensitivity threshold of the strip device of the present invention (Example 11). The device detects PAMG-1 in a sample based on the immobilization of the complex of labeled antibody M271-PAMG-1 in the test region 14.

Control Region. The device of the invention includes one standard control region 16 (FIGS. 1-2). This control region serves to confirm the proper operation of the device. It should be noted, however, that any alternative control-region designs may also be used with the device of the present invention.

The device with one control region includes the M271 antibody region 10 formed of a material which permits migration of antibodies and proteins therethrough, the M271 antibody region 10 including a labeled M271 antibody that is not immobilized therein and has a high specificity for PAMG-1, introduction to the M271 antibody pad region 10 of a fluid sample containing PAMG-1 resulting in the M271 antibody binding to PAMG-1 to form a antibody M271-PAMG-1 complex. The device also includes a test region 14 in fluid connection with M271 antibody region 10 which is formed of a material which permits migration of antibodies and proteins therethrough. The test region 14 also includes the M52 antibody immobilized in the test region 14 which has a binding affinity for PAMG-l. The M52 antibody is immunologically distinct from the M271 antibody such that the M271 and M52 antibodies can simultaneously bind to PAMG-1. Introduction of the fluid sample to the M271 antibody region 10 results in the migration of the antibody M271-PAMG-1 complex into the test region 14 where the antibody M271-PAMG-1 complex binds to the M52 antibody and is immobilized in test region 14 by the M52 antibody. The device detects PAMG-1 in a sample based on the immobilization of the labeled M271 antibody in the test region 14. When a low concentration of PAMG-1 is present in the sample, at least some of the labeled M271 antibodies migrates from the M271 antibody region 10 through the test region 14 to the control region 16. Anti-mouse anti-immunoglobulin antibodies are immobilized in the control region 16. Anti-immunoglobulin antibodies bind labeled M271 antibodies that stain the control region. If a high concentration of PAMG-1 is present in the sample, then only a low quantity of labeled M271 antibodies can approach the control region 16 and coloration of the control region may be too weak to become visible to the naked human eye. To prevent such a possibility, labeled mouse IgG immunoglobulin was added into M271 antibody region 10. This immunoglobulin does not bind PAMG-1 and migrates freely through M52 antibody test region 14 to the control region 16 where it is bound by anti-mouse antiglobulin antibodies and stains control region 16. The control region confirms the proper functioning of the device regardless of the concentration of PAMG-1 in the sample.

Yet another component of device of the present invention is a porous material that is in tight porous connection with material of test region. This part of device of the invention works as a pump that helps to move liquids, proteins and antibodies therethrough. Examples of detectable markers, which may be used for the labeling of mouse antibodies and IgG immunoglobulin include, but are not limited to stained particles, enzymes, dyes, and radioactive isotopes. In one embodiment, the detectable marker is a fluorescent dye. In yet another embodiment, the detectable markers are stained particles. In one embodiment, the M271 antibody, which is a labeled antibody and the labeled mouse immunoglobulin IgG are in a freeze-dried state.

The materials used in the various regions of the above-described device may be any combination of materials that permit the migration of antibodies and proteins therethrough. Examples of suitable materials include but are not limited to fiberglass, porous plastic, nitrocellulose, and filter paper.

The parts of device can be positioned in any functional combinations provided that in any embodiment of the device of this invention there is the selected pair of antibodies that detects a minimum background concentration of PAMG-1 in the vaginal secretion of pregnant women.

The device of this patent may optionally include a protective film covering at least a portion of the device. It can be transparent or not transparent and can have necessary trademark, informational marks/signs or arrows on its surface.

Detecting Fetal Membrane Ruptures

PAMG-1 exists in amniotic fluid at a concentration about at least 100 times greater than in the serum of pregnant women and at least 3000 greater than in vaginal secretion of pregnant women in the absence of fetal membranes rupture. As a result, even when a small amount of amniotic liquid (about $\frac{1}{100}$ of one drop per 1 ml of vaginal secretion) is dissolved in a vaginal secretion sample, a sufficient amount of PAMG-1 is present in this vaginal secretion sample to indicate that fetal membrane rupture has taken place. Further, because of the low concentration of PAMG-1 in blood serum, the insignificant admixture of blood serum to the sample (10-15%) does not affect the results produced by the devices and methods of the present invention.

Because the presence of amniotic fluid in a vaginal secretion is indicative of a fetal membrane rupture, the detection of PAMG-1 in vaginal secretion can also be used to detect fetal membrane rupture.

The method according to the present invention for detecting PAMG-1 in amniotic fluid is highly sensitive. For example, concentration of 0.05 ng/ml PAMG-1 can be detected (Examples 6, 7). Because the maximum concentration of PAMG-1 in serum is about 25 ng/ml, as compared to a minimum concentration of about 1680 ng/m in amniotic fluid, and because the background concentration of PAMG-1 in vaginal secretion is very low, about 0.2 ng/ml, a lower threshold level for PAMG-1 can be used in the method of the present invention for detecting the occurrence of amniotic fluid in the vagina. By using a lower detection threshold in the case of the present invention, most false results are avoided.

The devices and methods of the present invention are designed to avoid producing false results through the use of a pair of antibodies that is highly sensitive and specific to PAMG-1. Besides, the threshold of sensitivity of the device of the present invention may be accurately set up at the pre-defined level that is close to 5-7 ng/ml.

As a result, the devices and methods of the present invention are not influenced by the presence of vaginitis or other variables, which had a negative impact on the accuracy of prior methods for detecting fetal membrane ruptures. The maximum concentration of PAMG-1 in inflammation exudate is 3 ng/ml (Example 8, Tables 10, 11). The same concentration of PAMG-1 may occur if blood serum admixture to vaginal secretion does not exceed 10-15%. In addition, a large ratio of concentrations serum-to-amniotic PAMG-1 makes the devices and methods of the present invention significantly less likely to produce false positive results due to the presence of blood serum in vaginal secretions, even with a low PAMG-1-detection threshold. As described herein, the devices and methods can be adapted to be used easily in a rapid and convenient manner, thereby making it possible for the devices and methods to be used in outpatient conditions. For example, the method can be incorporated into an easy-to-use device that can be operated by a patient with little or no prior experience with the device. No special timing, dilution or matching of the sample concentrations prior to measurement is required in order to use the device. This makes the method and device highly reliable and not very susceptible to operator error. The method can also be designed to enable a simple yes/no determination of the presence of PAMG-1 in a sample and the presence of amniotic fluid in the vagina.

The present invention provides methods and devices for detecting a rupture in a fetal membranes based on the presence of PAMG-1 in the vaginal secretion of a pregnant woman. Consequently the method of the present invention for detecting fetal membrane ruptures simply includes the step of detecting PAMG-1 in the vaginal secretion the presence of PAMG-1 in the vaginal secretion indicating the occurrence of a fetal membrane rupture. The key part of the present invention is step-by-step selection of the pair of antibodies detecting very low background concentration of protein PAMG-1 in the vaginal secretion of pregnant women. The presence of PAMG-1 at low concentration in vaginal secretion could be expected since permeability of capillary wall for blood proteins depends on the posttranslational modifications of proteins and their interaction with other molecules (Marinaro J. A. et al, "O-glycosylation delays the clearance of human IGF-binding protein-6 from the circulation," in *European Journal of Enclocrinology*, May 2000, Vol. 142(5), p. 512; Schneeberger E. E., "Proteins and vesicular transport in capillary endothelium," *Fed. Proc.*, May 1983, Vol. 42(8), pp. 2419-24; Minshall R. D. et al, "Vesicle formation and trafficking in endothelial cells and regulation of endothelial barrier function," *Hislochem. Cell Biol.* February 2002, Vol. 117(2), pp. 105-12; Del Vecchio P. J. et al, "Endothelial monolayer permeability to macromolecules," in *Fed Proc* June 1987, Vol. 46(8), pp. 2511-2515; Siflinger-Birnbooim A et al, "Selectivity of the endothelial monolayer: effects on increase permeability," *Microvascular Research* November 1998, Vol. 36(3), pp. 216-227; Ghinea N., Milgrom, E. A., "New function for the LH/CG receptor: transcytosis of hormone across the endothelial barrier in target organs", in *Semin. Reproduce. Med.*, 2001, Vol. 19(1), pp. 97-101). Among the PAMG-1 molecules, which underwent the post-translational modifications, or established a non-covalent bond with another molecules, should be some whose penetration into the vaginal secretion is minimal. The concentration of such molecules in the vaginal secretion should be low. The low or high penetration of different molecules is due to the selective permeability of the capillary walls and selective secretory processes. Since it is known that the presence of amniotic fluid in the vaginal secretion of pregnant women is indicative of a fetal membrane rupture, the detection of PAMG-1 in the vaginal secretion can also be used to detect the presence of a fetal membrane rupture. Examples of methods and devices for detecting PAMG-1 in vaginal secretion include the methods and device described herein in more detail. The methods further include the step of detecting a fetal membrane rupture based on the detection of PAMG-1 in the sample of vaginal secretion are also described herein in more detail.

As has been discussed above, the methods and devices according to the present invention for detecting fetal membrane ruptures are highly specific, sensitive, and accurate. Sensitivity and accuracy are achieved by means of a wide gap between the low background concentration of PAMG-1 in the vaginal secretion of pregnant women and a much higher preset threshold of sensitivity of the device of the present invention, the threshold in turn being lower than the typical concentration of PAMG-1 in vaginal secretion at the time of a rupture of the fetal membrane, which creates a leakage of the amniotic fluid into vagina. The accurate set up of the threshold is in turn achieved by using at least one or more additional antibodies in test region 14 against PAMG-1 to set up precisely the predefined threshold of sensitivity of the device of the present invention (Example 9). Consequently, the methods and devices of the present invention are designed to avoid producing false negative and false positive results through the use of a highly specific pair of monoclonal antibodies M271 and M52 and at least one additional antibody M42. As a result, the accuracy of methods and devices is not adversely affected by the presence of vaginal infections or certain other variables which have reduced the accuracy of the methods of the Prior Art for detecting fetal membrane rupture. The preferred device and methods of the present invention for detecting PAMG-1 in the vaginal secretion of pregnant women are also designed to be easy, convenient and quick to use, thereby making it possible to use the device of the present patent on an outpatient basis. For example, the methods can be incorporated into an easy-to-use device which can be operated by a patient with little or no prior experience with the device. No special timing, dilution or matching of the sample concentrations prior to measurement is required in order to use the device. This makes the methods and device of the present invention for detecting fetal membrane ruptures highly reliable and not highly susceptible to operator errors. The results of clinical trials of the device of the invention are presented in Example 10. The measurement of the concentration of PAMG-1 in vaginal secretion at vaginitis is presented in Example 8. One can see from Example 8 that the maximum observed concentration of PAMG-1 in inflammation exudate is close to 3 ng/ml.

EXAMPLES

The following examples describe in further detail the isolation of PAMG-1 from amniotic fluid, the selection of a pair of antibodies against PAMG-1, the study of the specificity of such antibodies, and the concentration of PAMG-1 in inflammation exudate in vaginitis. These examples are provided to illustrate certain aspects of the present invention and they are not intended to limit the scope of the present invention.

Example 1

Concentration of PAMG-1 in Blood and Amniotic Fluid

The PAMG-1 concentration was measured in the blood serum of non-pregnant women, pregnant women (37-40 weeks of gestation), and in amniotic fluid (39-40 weeks of gestation) by ELISA using monoclonal antibody pairs generated as described in Example 3.

Antibodies M1, M271, M152 and M392, were sorbed to polystyrene in 0.05M carbonate-bicarbonate buffer at pH 9.5 for 18 hours at 6° C. (100 µl of antibody solution in each well). Non-specific sorption to the polystyrene was removed with a 1% solution of bovine serum albumin (BSA) in phosphate buffer saline (PBS) at pH 7.0, 200 µl in each well, incubated for one hour at 37° C.

One hundred µl of PAMG-1 antigen was added to each well at concentrations of 50, 25, 12, 6, 3, 1.5, and 0.7 ng/ml. The samples of blood serum or amniotic fluid were diluted in a buffer of 0.01% BSA and 0.05% Twin 20 in PBS. The diluted samples were added to the wells and the wells were incubated for one hour at 37° C. The reaction was developed by the solution of orthophenylenediamine in 0.05M citrate-phosphate buffer (pH 4.7), incubated for 20 minutes at 37° C. Optical density was read at the wavelength 492 nm.

A concentration of antibodies in the first layer and a concentration of conjugate were sought that resulted in the standard optical density curve for PAMG-1 with a maximum slope about 45 degrees (an increase by one optical unit corresponds to an increase of PAMG-1 concentration in the sample of 1 ng/ml), the upper limit (for the PAMG-1 concentration 50 ng/ml) of 1.5 optical units and zero concentration point not to exceed 0.1 optical units. The samples for investigation (sera, amniotic fluid, vaginal and cervical secretion) were frozen at −40° C. Each sample was tested three times. Sera were diluted to ⅕ of the original concentration. Amniotic fluid samples were diluted to 1/2000 of the original concentration. If the sample had an optical density above 1.5 units, the sample was diluted further and re-tested.

The data obtained are summarized below in Tables 1-3.

TABLE 1

Concentration of PAMG-1 (ng/ml) in the blood serum of non-pregnant women

| N | M1-M91 | M271-M52 | M152-M91 | M392-M371 |
|---|---|---|---|---|
| 1 | 20 | 0 | 15 | 12 |
| 2 | 20 | 0 | 15 | 13 |
| 3 | 60 | 5 | 50 | 46 |
| 4 | 50 | 7 | 48 | 50 |
| 5 | 40 | 4 | 30 | 34 |
| 6 | 64 | 15 | 50 | 56 |
| 7 | 20 | 7 | 15 | 14 |
| 8 | 48 | 8 | 35 | 30 |
| 9 | 15 | 0 | 10 | 14 |
| 10 | 40 | 5 | 20 | 35 |

TABLE 2

Concentration of PAMG-1 (ng/ml) in the blood serum of pregnant women (37-40 weeks of gestation).

| N | M1-M91 | M271-M52 | M152-M91 | M392-M371 |
|---|---|---|---|---|
| 1 | 90 | 8 | 70 | 50 |
| 2 | 100 | 15 | 90 | 75 |
| 3 | 105 | 16 | 95 | 75 |
| 4 | 120 | 22 | 100 | 94 |
| 5 | 100 | 12 | 98 | 90 |
| 6 | 98 | 14 | 95 | 80 |
| 7 | 104 | 20 | 90 | 80 |
| 8 | 98 | 25 | 75 | 60 |
| 9 | 64 | 5 | 55 | 40 |
| 10 | 70 | 10 | 60 | 40 |

TABLE 3

Concentration of PAMG-1 (ng/ml) in the amniotic fluid (39-40 weeks of gestation).

| N | M1-M91 | M271-M52 | M152-M91 | M392-M371 |
|---|---|---|---|---|
| 1 | 8,000 | 1,680 | 6,400 | 5,000 |
| 2 | 12,000 | 8,000 | 6,000 | 5,000 |
| 3 | 10,000 | 6,000 | 7,000 | 6,000 |
| 4 | 6,000 | 2,000 | 5,000 | 4,500 |
| 5 | 8,000 | 12,000 | 5,800 | 5,000 |
| 6 | 7,000 | 20,000 | 5,000 | 5,000 |
| 7 | 6,000 | 2,000 | 4,000 | 3,000 |
| 8 | 75,000 | 8,000 | 5,000 | 4,700 |
| 9 | 2,000 | 3,000 | 1,440 | 1,500 |
| 10 | 40,000 | 13,000 | 36,000 | 25,000 |

Example 2

Isolation of PA MG-1

D. Petrunin proposed the modified method of isolation of PAMG-1 in 1980 (Petrunin, D. D., Kozlyaeva, G. A., Tatarinov, Yu. S., Shevchenko, O. P., Bulletin of Experimental Biology and Medicine, No 5, p. 558, 1980 (in Russian)). The steps of the scheme are outlined in Table 4 below.

TABLE 4

Steps of isolation of PAMG-1

| Steps of Isolation | Purity % | Yield % |
|---|---|---|
| Amniotic fluid 16-25 weeks pregnancy | 4 | 100 |
| Precipitation by 0.5% lanthanum chloride | 25 | 90 |
| Precipitation by ammonium sulphate at 50% saturation | 35 | 70 |
| Precipitation by lithium sulphate at 60% saturation | 60 | 60 |
| Reverse Phase Chromatography Separation | 90 | 30 |

PAMG-1 was separated from the amniotic fluid at 16 to 25 weeks of gestation. The fluid was obtained from women whose pregnancy was terminated due to medical considerations. We added 10% solution of lanthanum chloride at the volumetric ratio 20:1 (so that its final concentration was 0.5%) to the amniotic fluid and kept at 4° C. for 18 hours. Precipitate formed and was separated by centrifugation at 8,000 rpm for 30 min. We dissolved the precipitate in the saturated solution of $Na_2HPO_4$ and separated the precipitate of insoluble lanthanum salts produced in the process by centrifugation at 8,000 rpm for 30 min. We fractionated the resulting solution with 50% saturated ammonium sulphate by incubating at 4° C. for 18 hours and dissolved the resulting precipitate in the distilled water in such a way as to restore in both cases the volume of the dissolved precipitation fractions to the initial volume of the amniotic fluid. Then we precipitated the solution by 60%-saturated lithium sulphate and dissolved the precipitate in a small amount of distilled water. After dialysis, we adsorbed the admixtures with calcium pyrophosphate by adding an equal volume of moisture absorbent to the protein solution, intermixing and incubating for 10-15 min., and separated the absorbent by centrifugation.

Example 3

Production of the Stable Hybrid Lines of Present Invention

Hybridoma Experiment 1. Lymphocytes from popliteal lymph nodes of 5 BALB/c mice were used. Mice were immunized by five injections of PAMG-1 in foot pads. Each injection consisted of 100 µg of PAMG-1 and Freund's Complete Adjuvant in a 1: I ratio. After the cell fusion, the cells were seeded in 1152 wells. Total of 363 primary hybridomas were tested, 38 of them were PAMG-1-positive. Then the specificity of monoclonal antibodies was tested by studying their cross-reactive binding of proteins—alpha-2-microglobulin of fertility, human chorionic gonadotropin, trophoblastic beta-1-glycoprotein, human placental,lactogen, alpha-fetoprotein, and human serum albumin. Fourteen primary hybridomas were selected whose monoclonal antibodies were not cross-reactive to other proteins. Then a method of limiting dilutions was used to clone twice the primary PAMG-1-specific hybridomas. Finally, five clones were selected that were apparently the most stable and productive producers of monoclonal antibodies M1, M38, M42, M52, M91.

Hybridoma Experiment 2. Lymphocytes from the spleen of 5 mice were used. Mice were immunized five times by intraperitoneal injection of 100 mg of PAMG-1. Each injection consisted of PAMG-1 and Freund's Complete Adjuvant in a I: I ratio. 1344 wells were used and 562 hybridomas were tested. Of these, 45 turned out PAMG-1-positive, and 19 were not cross-reactive to the other proteins, e.g. PAMG-1-specific. Not cross-reactive hybridomas were cloned twice and 6 clones that proved to be most stable and intensive producers of monoclonal antibodies M122, M152, M211, M271, M371 and M392 were selected for further use.

Therefore, 11 monoclonal antibodies were created to PAMG-1 and then the pair of these antibodies was selected that detected a minimum background concentration of PAMG-1 in the vaginal secretion of pregnant women, as described in Example 4.

Specific Cell Lines According to the Present Invention

Antibodies M271 and M52 are produced by hybridoma cell lines M271 and M52 respectively. Cell lines producing the monoclonal antibodies referred to herein as M271 and M52, and additionally M42, produce monoclonal antibodies used to set up and adjust a threshold of sensitivity of the device as described below.

Table 5 reports the results for production of hybridomas from two trials.

TABLE 5

|  | Total | 1st hybridoma | 2nd hybridoma |
|---|---|---|---|
| Wells, total | 2496 | 1152 | 1344 |
| Number of primary hybridomas | 925 | 363 | 562 |
| Number of hybridomas producing PAMG-1 - positive monoclonal antibodies | 83 | 38 | 45 |
| Number of hybridomas producing PAMG-1 - specific monoclonal antibodies | 33 | 14 | 19 |

TABLE 5-continued

|  | Total | 1st hybridoma | 2nd hybridoma |
|---|---|---|---|
| Number of stable hybridoma lines producing monoclonal antibodies, chosen for further studies | 11 | 5 | 6 |

Example 4

Selection of the Pair of the Monoclonal Antibodies Detecting a Minimum Concentration of PAMG-1 in Vaginal Secretion of Pregnant Women PAMG-1 at a concentration of 1 µg/ml in 0.05M carbonate-bicarbonate buffer, pH 9.5, was sorbed to polystyrene plates by incubation for 18 hours at 4° C. The antibodies listed in Table 6 below were added to the wells in serial dilutions starting from 3 mg/ml. The plates were then incubated for one hour at 37° C. An antibody conjugate of rabbit anti-mouse anti-IgG antibodies labeled by horseradish peroxidase was added to the wells. The reaction was developed by the solution of orthophenylenediamine in 0.05M citrate-phosphate buffer (pH 4.7), incubated for 20 minutes at 37° C. The monoclonal antibody titer was quantitated.

TABLE 6

Affinity of binding of PAMG-1 at concentration 1 µg/ml by monoclonal antibodies of the present invention.

| MAb | Titre at 1 µg/ml concentration of PAMG-1 |
|---|---|
| M1 | 1:900,000 |
| M42 | 1:1,000,000 |
| M52 | 1:1,000,000 |
| M91 | 1:1,000,000 |
| M122 | 1:2,000,000 |
| M152 | 1:1,000,000 |
| M392 | 1:1,000,000 |
| M371 | 1:400,000 |
| M271 | 1:3,000,000 |
| M38 | 1:50,000 |
| M211 | 1:50,000 |

Concentrations of monoclonal antibodies shown in Table 6 are the minimum concentrations at which the antibodies bind PAMG-1, provided concentration of PAMG-1 in the solution is The lower the concentration is, the higher an antibody's ability to detect minimal concentrations of PAMG-1. Monoclonal antibodies M271 and M52 were chosen to develop a high sensitivity ELISA for PAMG-1.

The monoclonal antibody M271 did not show cross-reactivity in ELISA with the following individual proteins of the amniotic fluid: fertility alpha-2-microglobulin; human chorionic gonadotropin; human placental lactogen; trophoblastic beta-1-glycoprotein; alpha fetoprotein; human serum albumin.

In addition to that, in the experiments with columns M271 antibodies were fixed on the sepharose and the non-diluted amniotic fluid was passed through the column. An eluate obtained from the columns after electrophoresis has shown one band corresponding to a molecular mass that matched the molecular mass of PAMG-1 (28-30 kDa). The highly specific monoclonal antibody M271 was placed in the pad of the lateral flow strip device of the present invention.

In contrast to the antibody M271, the antibody M52 was cross-reactive in ELISA with IGFBP-3 protein that is abundant in serum and amniotic fluid. The concentration of the non-glycosilated IGFBP-3 measured in the vaginal secretion was about 600 ng/ml (Example 9). In the experiments with strip device of present invention IGFBP-3 at this concentration did not inhibit recognition of PAMG-1 taken at concentration 5 ng/ml.

Example 5

High-Sensitivity ELISA Test for Placental α1-Microglobulin

PAMG-1 could not be detected in vaginal secretion using standard ELISA and the M271–M52 antibody pair. To permit detection, the sensitivity of the ELISA was increased by decreasing the concentration of PAMG-1 required for detection to 0.05 ng/ml.

A sandwich immunoassay system with antibodies M217–M52, which demonstrated sensitivity 50 picogram per milliliter (0.05 ng/ml), was developed:

1st layer: monoclonal antibodies M271, concentration 6 μg/ml, in the carbonate-bicarbonate buffer, pH 9.5.

2nd layer: PAMG-1, concentrations 3200, 1600, 800, 400, 200, 100, 50 pg/ml, and cervical and vaginal secretions diluted to 1/2 concentration, on the buffer with pH=7.0.

3rd layer: conjugate M52 on the buffer at dilution 1/1000.

The increase in sensitivity was obtained by varying the 1st and 3rd layers. In contrast to the high-sensitivity system, in the regular system with sensitivity 1 ng/ml the 1st layer was formed with concentration of M271 of 10 to 20 μg/ml, and dilution of the conjugate (M52 labeled with horseradish peroxidase) was 1/40,000.

A standard calibration curve was obtained. It is shown in Table 7 below, where PAMG-1 concentration is given in picogram per milliliter (pg/ml) and optical density of observed coloration E at wavelength 450 nm is in standard non-dimensional units.

TABLE 7

Calibration Curve of High Sensitivity ELISA.

| PAMG-1 pg/ml | | | | | | | |
|---|---|---|---|---|---|---|---|
| 3200 | 1600 | 800 | 400 | 200 | 100 | 50 | 0 |

| E 450 nm | | | | | | | |
|---|---|---|---|---|---|---|---|
| 2.000 | 1.725 | 1.432 | 1.130 | 0.851 | 0.600 | 0.304 | 0.051 |

Example 6

PAMG-1 in the Vaginal Secretions of Pregnant Women

TABLE 8

Concentration of PAMG-1 (ng/ml) in the vaginal secretion of pregnant women. Measurements are conducted using different pairs of monoclonal antibodies against PAMG-1 (29-41 weeks of gestation).

| N | Weeks of gestation | M1-M91 | M271-M52 | M152-M91 | M392-M371 |
|---|---|---|---|---|---|
| 1 | 29 | 25 | 0.15 | 5 | 6 |
| 2 | 34 | 50 | 0.1 | 10 | 8 |
| 3 | 37-38 | 70 | 0.22 | 30 | 15 |
| 4 | 37-38 | 60 | 0.06 | 25 | 10 |
| 5 | 33-34 | 30 | 0.05 | 13 | 5 |
| 6 | 29-30 | 45 | 0.05 | 13 | 5 |
| 7 | 33 | 50 | 0.16 | 14 | 10 |
| 8 | 30 | 60 | 0.09 | 15 | 12 |
| 9 | 39-40 | 84 | 0.21 | 28 | 18 |
| 10 | 35-36 | 90 | 0.13 | 30 | 19 |
| 11 | 38-39 | 90 | 0.13 | 30 | 20 |
| 12 | 38 | 65 | 0.15 | 25 | 15 |
| 13 | 31 | 95 | 0.35 | 45 | 30 |
| 14 | 39 | 44 | 0.05 | 10 | 5 |
| 15 | 29-30 | 80 | 0.2 | 28 | 12 |
| 16 | 40-41 | 58 | 0.078 | 24 | 10 |
| 17 | 37 | 90 | 0.15 | 40 | 30 |
| 18 | 29-30 | 70 | 0.4 | 15 | 12 |
| 19 | 29 | 65 | 0.64 | 15 | 12 |
| 20 | 30 | 80 | 0.1 | 22 | 20 |

Following the measurement of the minimum concentrations, each antibody was labeled with horse radish peroxidase. In the ELISA test, non-labeled antibodies at a concentration of 10 μg/ml were introduced in the wells of the plates. Then, PAMG-1 at concentrations of 50, 100, 200, 400, 800, 1600, 3200 pg/ml were introduced for a second layer on the plastic. At last, the conjugate of one of the other antibodies was introduced into each well of the plate. The following antibodies that work in pairs were selected (shown here as antibody-conjugate): M1–M91; M271–M52; M152–M91; M392–M371.

These pairs of antibodies were used to measure PAMG-1 concentration in the vaginal secretion of pregnant women. Finally, the pair M271–M52 antibodies was picked, for which the measured concentration of PAMG-1 in the vaginal secretion was the lowest. The concentration of PAMG-1 for the M271–M52 pair was measured using highly sensitive ELISA. The selected pair M271–M52 and a few other pairs were used to measure the concentration of PAMG-1 in the amniotic fluid and in the blood serum of non-pregnant and pregnant women (Example 1, supra).

Example 7

PAMG-1 in the Vaginal and Cervical Secretions of Pregnant Women

TABLE 9

Concentration of PAMG-1, picogram per milliliter (pg/ml), in the cervical and vaginal secretion of pregnant women. Normal gestation in the table below indicates the absence of any diagnosed deviations from normal course of gestation. PAMG-1 concentration was measured by highly sensitive ELISA using the M271-M52 antibody pair.

| No | PAMG-1, pg/ml in cervical secretion | PAMG-1 pg/ml in vaginal secretion | Week of Gestation | Notes |
|---|---|---|---|---|
| 1 | 230 | 150 | 29 | Normal gestation |
| 2 | 220 | 100 | 34 | Normal gestation |
| 3 | 340 | 150 | 38 | Erosion, blood in cervical secretion |
| 4 | 110 | 220 | 37-38 | Normal gestation |
| 5 | 100 | 60 | 37-38 | Normal gestation |
| 6 | 350 | 78 | 40-41 | Blood in cervical secretion |
| 7 | 60 | 400 | 29-30 | Threatened abortion |
| 8 | 50 | 50 | 33-34 | Normal gestation |
| 9 | 180 | 50 | 29-30 | Normal gestation |

TABLE 9-continued

Concentration of PAMG-1, picogram per milliliter (pg/ml), in the cervical and vaginal secretion of pregnant women. Normal gestation in the table below indicates the absence of any diagnosed deviations from normal course of gestation. PAMG-1 concentration was measured by highly sensitive ELISA using the M271-M52 antibody pair.

| No | PAMG-1, pg/ml in cervical secretion | PAMG-1 pg/ml in vaginal secretion | Week of Gestation | Notes |
|---|---|---|---|---|
| 10 | 470 | 150 | 37 | Blood in cervical secretion |
| 11 | 600 | 640 | 29 | Threatened abortion |
| 12 | 150 | 160 | 33 | Normal gestation |
| 13 | 170 | 90 | 30 | Normal gestation |
| 14 | 122 | 210 | 39-40 | Oligohydramnios, gestosis |
| 15 | 300 | 50 | 39 | Gestosis, vaginitis |
| 16 | 56 | 130 | 35-36 | Disorder of retroplacental blood supply |
| 17 | 120 | 130 | 38-39 | Anemia |
| 18 | 1000 | 5000 | 30-31 | Amniotic fluid leak |
| 19 | 400 | 200 | 29-30 | Threatened abortion |
| 20 | 800 | 350 | 31 | Gestosis |

Example 8

PAMG-1 in the Vaginal Secretions of Pregnant Women with Vaginitis

TABLE 10

Concentration of placental alpha-1-microglobulin in the vaginal secretion of pregnant women with vaginitis. Measurements were made using a non-highly sensitive ELISA.

| No of Patient | PAMG-1 (ng/ml) |
|---|---|
| 1 | 1.2 |
| 2 | 2.0 |
| 3 | 0 |
| 4 | 2.5 |
| 5 | 1.5 |
| 6 | 1.9 |
| 7 | 1.5 |
| 8 | 2.0 |
| 9 | 1.4 |
| 10 | 1.2 |
| 11 | 1.0 |
| 12 | 0 |
| 13 | 0 |
| 14 | 3.0 |
| 15 | 1.5 |

TABLE 11

Concentration of placental alpha-1-microglobulin in the vaginal secretion of pregnant women with vaginitis.

| N | Name (Second initial, First initial Middle initial) | Diagnosis | Device of present invention result ("−" is "negative") | ELISA ng/ml |
|---|---|---|---|---|
| 1 | Ch., G. A. | 40 week gestation. Vaginitis. | − | 1.2 |
| 2 | To., E. N. | 38 week gestation. Fetal hypotrophy. Vaginitis. | − | 2.0 |
| 3 | Ne., N. N. | 33 week gestation. Pyelonephritis. Vaginitis. | − | 0 |
| 4 | St., A. G. | 38 week gestation. Contracted pelvis. Vaginitis. | − | 2.5 |
| 5 | So., T. N | 40 week gestation. Vaginitis. | − | 1.5 |
| 6 | Ch., O. G. | 29-30 week gestation. Risk of premature labor. Vaginitis. | − | 1.9 |
| 7 | Ry., V. V. | 29 week gestation. Signs of labor. Vaginitis. | − | 1.5 |
| 8 | Ma., K. S. | 38 week gestation. Cervical erosion. Vaginitis. | − | 2.0 |
| 9 | St., L. E. | 38-39 week gestation. Contracted pelvis. Cervical erosion. Vaginitis. | − | 1.4 |
| 10 | La., V. S. | 36-37 week gestation. Risk of premature labor. Vaginitis. | − | 1.2 |
| 11 | Si., M. A. | 39 week gestation. Nephropathy. Anaemia. Vaginitis. | − | 1.0 |
| 12 | Sh., S. V. | 37-38 week gestation. Nephropathy. Vaginitis. | − | 0 |
| 13 | Ab., R. V. | 36-37 week gestation. Risk of premature labor. Vaginitis. | − | 0 |
| 14 | Gu., E. K. | 36 week gestation. Risk of premature labor. Vaginitis. | − | 3.0 |
| 15 | Ro., N. V. | 35 week gestation. Vaginitis. | − | 1.5 |
| 16 | De., S. V. | 32 week gestation. Cervical erosion. Vaginitis. | − | 0 |
| 17 | Zd., I. V. | 35 week gestation. Risk of premature labor. Cervical erosion. Vaginitis. | − | 1.0 |
| 18 | Ko., T. V. | 24 week gestation. Risk of premature labor. Vaginitis. | − | 0 |
| 19 | Ma., I. V. | 36 week gestation. Risk of premature labor. Vaginitis. | − | 0 |
| 20 | Io., I. V. | 40 week gestation. Cervical erosion. Vaginitis. | − | 0 |
| 21 | Ma., S. | 39 week gestation. | − | 0 |
| 22 | Ve., E. L. | 38 week gestation. Cervical erosion. Vaginitis. | − | 0 |
| 23 | St., I. N. | 36 week gestation. Nephropathy. Vaginitis. | − | 0 |
| 24 | Ro., V. A. | 39-40 week gestation. Anemia. Vaginitis. | − | 0 |
| 25 | Pu., T. A. | 38-39 week gestation. | − | 0 |
| 26 | Tu., Y. A. | 21 week gestation. Suspected PROM. | − | 0 |
| 27 | No., G. V. | 22 week gestation. Risk of termination. | − | 0 |
| 28 | Ma., E. V. | 31-32 week gestation. Pyelonephritis. Vaginitis. | − | 0 |
| 29 | St., I. V. | 36 week gestation. Risk of termination. | − | 0 |
| 30 | Ka., K. P. | 32 week gestation. Nephropathy. | − | 0 |

Example 9

Modifications of Strip Device Characteristics

In the first experiment, M52 MAb solutions were prepared in concentrations 1, ½, ¼, ⅛, 1/16 and 1/32 mg/ml. Each solution was placed into one strip device. A mixture of the three MAb (M52, M271, M42) was also diluted to the concentrations 1, ½, ¼, ⅛, 1/16 and 1/32 of the original and each diluted solution was introduced in a separate strip device. Then, PAMG-1 containing solution in concentration 50 ng/ml was added to each of the 12 strip devices. The solution of pure M52 antibody made the colored band in the test region visible at a concentration of ⅛, and in the MAb mixture the colored band became visible at a concentration of ½. Therefore, the mixture of MAb inhibits the attachment of PAMG-1 molecules, thereby adjusting the visibility of the band.

Monoclonal antibodies at concentrations: M52: 0.8 mg/ml, M271: 0.1 mg/ml, and M42: 0.1 mg/ml were placed into the test region of many strip devices. Then, PAMG-1 in one of a broad range of concentrations, from 12800 ng/ml to 7 ng/ml, and at 1 ng/ml was added to the test region of each of the strip devices of the present invention. The test band could be seen by a human eye in the range of PAMG-1 concentrations from 12800 ng/ml to 7 ng/ml, and it could not be seen at the concentration of 1 ng/ml. At the same time, when pure M52 solution at the same concentration was used, the test strip could be seen in the entire range of PAMG-1 concentrations, including 1 ng/ml, although the intensity at 1 ng/ml was low. This strongly increased the likelihood of false positive result in patients with certain medical conditions such as inflammation.

1. Adjustment of the Sensitivity of Strip Device of the Present Invention with a Combination of Two Antibodies in Test Region.

In the first investigation, only M52 antibodies (in a concentration of 0.4 mg/ml) were introduced into the test region. In the second investigation, M52 antibodies (in a concentration of 0.4 mg/ml) and M271 antibodies (in a concentration of 0.4 mg/ml) were introduced into the test region. M271 antibody conjugated with gold particles was introduced into the pad reuion in a concentration chosen so that the optical density was ten at the wavelength of 510 nm. This conjugate was introduced into the pad in a solution of 10% saccharose and 2% casein. PAMG-1 was titered to concentrations of 20, 10, 5, and 1 ng/ml.

In the tables below, the numbers are relative optical density indices measured by the Sigma Scan program on a scanner. M271 antibodies are in the pad; a combination M271+M52 is in the test region. "+" indicates that the test strip is visible (colored enough to be detected by a human eye), "−" indicates that the test band cannot be detected by a human eye.

|  | Concentration of PAMG-1, ng/ml | | | |
| --- | --- | --- | --- | --- |
|  | 20 | 10 | 5 | 1 |
| MAb M52 Visible | 62 | 58 | 39 | 2 |
|  | + | + | + | − |
| MAb M52 + M271 Visible | 82 | 8 | 2 | 4 |
|  | + | − | − | − |

The sensitivity of the test changed from 5 ng/ml in the first investigation to 20 ng/ml in the second investigation. One may conclude that by adding MAb M271 to the test region, fourfold inhibition of the sensitivity was obtained.

2. Adjustment of the Color Intensity of a Test Band in the Strip Device with a Combination of Two Antibodies In the first investigation, only M52 antibodies (at a concentration of 0.8 mg/ml) were introduced into the test region. In the second investigation, M52 antibodies (0.8 mg/ml), M271 antibodies (0.7 mg/ml) and M42 antibodies (0.8 mg/ml) were introduced into the test region. The mixture of antibodies for the test region was prepared as follows: 14 μl (microliter) of M52 antibody solution, at concentration 8.6 mg/ml, was mixed with 7 μl of M42 solution, at concentration 13.9 mg/ml, and with 3 μl of M271 solution, at concentration 10.9 mg/ml. Then the buffer was added to the total volume of 150 μl and the solution was introduced into the strip device.

In the table below, the relative optical densities are shown.

|  | Concentration of PAMG-1, ng/ml | | | | | |
| --- | --- | --- | --- | --- | --- | --- |
|  | 50 | 25 | 12 | 6 | 3 | 1.5 |
| MAb M52 Visible | 17 | 13 | 9 | 5 | 2 | 0 |
|  | + | + | + | + | − | − |
| MAb M271 + M52 + M42 Visible | 25 | 18 | 13 | 3 | 0 | 0 |
|  | + | + | + | − | − | − |

The slope (gradient) of the optical density curve differed between the first and second investigations. At a PAMG-1 concentration of 12 ng/ml, the colored line on the strip in the second investigation was brighter than in the first investigation. At a PAMG-1 concentration of 6 ng/ml, the colored line on the strip was visible in the first investigation but invisible in the second investigation.

With a combination of antibodies visually brighter bands were observed. Therefore, despite of nearly the same sensitivity, the intensity of coloration observed by a human eye was different.

3. The Adjustment of Sensitivity and Slope of the Coloration Intensity Curve of the Device of Present Invention Using a Combination of Four Antibodies.

In the table below "+" stays for visible test band, "−"—the test band cannot be detected by a human eye.

|  | Concentration of PAMG-1, ng/ml | | | | | | |
| --- | --- | --- | --- | --- | --- | --- | --- |
|  | 0 | 1 | 2.5 | 5 | 10 | 25 | 50 |
| MAb M52 + M42 + M172 | − | − | − | − | + | + | + |
| MAb M271 + M52 + M42 + M122 | − | − | − | + | + | + | + |

Therefore, by combining antibodies one can adjust the sensitivity of the test.

Example 10

Results of Clinical Trials

Study Protocol

Patients were evaluated by "Clinical assessment"-control and by the device of the present Invention.

Inclusion Criteria:
1) Gestational age 20.0-41.0 weeks.
2) Patient reporting signs or symptoms suggestive of PROM or PPROM.
3) No digital vaginal examinations until specimens are obtained to evaluate the patient for PROM or PPROM.
4) Patient consents to a sterile speculum exam for the purpose of collection of standard clinical assessment (pooling, nitrazine, ferning) and sterile swabs for the PAMG-1 assay.

Exclusion Criteria:
1) Active vaginal bleeding from any source
2) Placenta previa Statistical analysis available on 192 patients as of Dec. 15, 2000 from Sharp Memorial Mary Birch Hospital for Women (San Diego) and from Summit Medical Center (Oakland).

In two patients out of 192, the device of present invention gave a positive response while standard clinical assessment did not show any evidence of PROM. These two cases, therefore, were originally accounted as a false positive result from the device of the present invention (see "Not Corrected" data below). However, the symptoms of PROM rapidly developed in both patients within hours after testing. The diagnosis of PROM was confirmed in a second clinical assessment, and both results of the device of the present invention were deemed true positive ("Corrected" column below represents the final trial data).

| Combined Data (Not corrected) Dx PROM | Combined Data (Corrected) Dx PROM |
|---|---|
| a = 84, b = 5, c = 2, d = 101<br>Sensitivity = a/(a + c) = 84/(84 + 2) = 97.7%<br>Specificity = d/(b + d) = 101/(5 + 101) = 95.3%<br>PPV = a/(a + b) = 84/(84 + 5) = 94.4%<br>NPV = d/(d + c) = 101/(101 + 2) = 98.1% | a = 88, b = 1, c = 0, d = 103<br>Sensitivity = 84/(84 + 0) = 100%<br>Specificity = 103/(1 + 103) = 99%<br>PPV = 88/(88 + 1) = 99%<br>NPV = 103/(103 + 0) = 100%, | where
a is number of true positive cases observed;
b is number of false negative cases observed;
c is number of false positive cases observed;
d is number of true negative cases observed;

$$\text{Sensitivity} = \frac{a}{a+c}; \text{Specificity} = \frac{d}{b+d};$$

Positive Predictive Value:

$$PPV = \frac{a}{a+b};$$

Negative Predictive Value:

$$NPV = \frac{d}{d+c};$$

True Positive is the number of positive responses by the device of the present invention, PROM is confirmed by the subsequent clinical assessment, True Negative is the number of negative responses confirmed by the subsequent clinical assessment, False Positive is the number of positive responses, but PROM is not confirmed by the subsequent clinical assessment, False Negative is the number of negative responses, but PROM is confirmed by the subsequent clinical assessment.

TABLE 12

Trials of the device of the present invention (Lot C 98-0007) in the Third Maternity Hospital of Moscow, Russian Federation, Obstetrics and Gynecology Department #2.

| N | Name (Second initial, First initial, Middle initial) | Diagnosis | Amnisure results | Notes |
|---|---|---|---|---|
| 1 | Ser., L. B. | 17 week gestation. Threatened abortion. Vaginitis | Negative | Clinical observation: no leak |
| 2 | Ga., L. A. | 17 week gestation. Threatened abortion | Negative | Clinical observation: no leak |
| 3 | Kuz., M. B. | 23 week gestation. pH-negative. Blood. | Negative | No leak |
| 4 | Bul., M. V. | 39 week gestation. Suspected leak. Vaginitis | Positive | Clinical observation: increased vaginal discharge. Further observation: positive test confirmed (more discharge, start of labor). |
| 5 | Kra., E. U. | 40 week gestation. Gestosis. Amniotomy | Negative | Clinical observation: no leak |
| 6 | Mel., N. V. | 39 week gestation. Gestosis. Urolithic disease | Negative | Clinical observation: no leak |
| 7 | Buh., S. N. | 29 week gestation. Hypertension | Negative | Clinical observation: no leak |
| 8 | Niv., I. P. | 27-28 week gestation. Threatened abortion | Negative | Clinical observation: no leak |
| 9 | Aik., A. | 35 week gestation. Threatened abortion. Vaginitis | Negative | Clinical observation: no leak |
| 10 | Yak., L. A. | 40 week gestation. | Negative | Clinical observation: no leak |
| 11 | Kis., G. V. | 33 week gestation. Threatened abortion. Vaginitis | Negative | Clinical observation: no leak |
| 12 | Koch., L. A. | 34 week gestation. Suspicion of a leak | Negative | Clinical observation: no leak |

TABLE 12-continued

Trials of the device of the present invention (Lot C 98-0007) in the Third Maternity Hospital of Moscow, Russian Federation, Obstetrics and Gynecology Department #2.

| N | Name (Second initial, First initial, Middle initial) | Diagnosis | Amnisure results | Notes |
|---|---|---|---|---|
| 13 | Bai., S. A. | 32 week gestation. Threatened abortion. Gestosis | Negative | Clinical observation: no leak |
| 14 | Mor. I. S. | 32 week gestation. Threatened abortion. Vaginitis | Negative | Clinical observation: no leak |
| 15 | Ugr., T. I. | 32-33 week gestation. Gestosis. Low amniotic fluid | Negative | Clinical observation: no leak |
| 16 | Pav., N. A. | 22-23 week gestation. Gestosis. Vaginitis | Negative | Clinical observation: no leak |
| 17 | Bog., T. I. | 29 week gestation. Threatened abortion | Negative | Clinical observation: no leak |
| 18 | Var., T. I. | 32 week gestation. Gestosis | Negative | Clinical observation: no leak |
| 19 | Dal., O. V. | 35 week gestation. Gestosis. Vaginitis | Negative | Clinical observation: no leak |
| 20 | Koz., O. A. | 40 week gestation. | Negative | Clinical observation: no leak |
| 21 | Sen., S. G. | 12-13 week gestation. Threatened abortion | Negative | Clinical observation: no leak |
| 22 | Pol., E. A. | 21 week gestation. Threatened abortion | Negative | Clinical observation: no leak |
| 23 | Ber., L. M. | 24 week gestation. Threatened abortion | Negative | Clinical observation: no leak |
| 24 | Ard., V. M. | 39 week gestation. Acute gestosis. Placental insufficiency | Negative | Clinical observation: no leak |
| 25 | Aki., A. | 8 week gestation. Gestosis. Vaginitis | Negative | Clinical observation: no leak |

TABLE 13

Trials of the device of the present invention (Lot C 98-0007) in the Third Maternity Hospital of Moscow, Russian Federation.

| N | Name | Diagnosis | Amnisure results | Notes |
|---|---|---|---|---|
| 1 | Fan., E. A. | 38 week gestation. Edema | Negative | Clinical observation confirmed the test results |
| 2 | Sem., Z. D. | 36 week gestation. Gestosis | Negative | Clinical observation confirmed the test results |
| 3 | Tab., N. V. | 36-37 week gestation. Threatened abortion | Negative | Clinical observation confirmed the test results |
| 4 | Zah., O. P. | 35 week gestation. Edema. Vaginitis | Negative | Clinical observation confirmed the test results |
| 5 | Dem., O. V. | 38-39 week gestation. Edema | Negative | Clinical observation confirmed the test results |
| 6 | Vul., D. V. | 32 week gestation. Threatened abortion. Vaginitis | Negative | Clinical observation confirmed the test results |
| 7 | Klo., V. V. | 38-39 week gestation. Edema. Pyelonephritis. Cervical erosion | Negative | Clinical observation confirmed the test results |
| 8 | Bor., E. A. | 35-36 week gestation. Disturbance of placental circulation | Negative | Clinical observation confirmed the test results |
| 9 | Jer., E. A. | 40-41 week gestation. | Negative | Clinical observation confirmed the test results |
| 10 | Vik., N. P. | 41-42 week gestation. Pyelonephritis. Edema. Vaginitis | Negative | Clinical observation confirmed the test results |
| 11 | Tul., O. S. | 35-36 week gestation. Gestosis. Obesity | Negative | Clinical observation confirmed the test results |

TABLE 13-continued

Trials of the device of the present invention (Lot C 98-0007) in the Third Maternity Hospital of Moscow, Russian Federation.

| N | Name | Diagnosis | Amnisure results | Notes |
|---|---|---|---|---|
| 12 | Med., T. E. | 38-39 week gestation. Varicosis | Negative | Clinical observation confirmed the test results |
| 13 | Kuz., T. A. | 39-40 week gestation. | Negative | Clinical observation confirmed the test results |
| 14 | Kab., E. M. | 39-40 week gestation. Edema. Polyhydramnios | Negative | Clinical observation confirmed the test results |
| 15 | Che., E. V. | 39-40 week gestation. Edema. Anemia | Negative | Clinical observation confirmed the test results |
| 16 | Tih., T. Y. | 40 week gestation. Pre-eclampsia | Negative | Clinical observation confirmed the test results |
| 17 | Bah., N. I. | 39-40 week gestation. Prognostic of delivery. Suspected leak | Negative | Clinical observation confirmed the test results |
| 18 | Gol., N. V. | 38-39 week gestation. Fetal hypoxia | Negative | Clinical observation confirmed the test results |
| 19 | Gri., O. V. | 25 week gestation. Threatened abortion. | Negative | Clinical observation confirmed the test results |

TABLE 14

Trials of the device of the present invention (Lot C 98-0007) in the Third Maternity Hospital of Moscow, Russian Federation.

| N | Diagnosis | Amnisure results | Notes |
|---|---|---|---|
| 1 | 40 week gestation. Giant fetus. Suspicion of leak | Positive | Labor pains, labor activity developed in 4 hours. Evident leak observed |
| 2 | 34 week gestation. Threatened abortion | Negative | Clinical observation for 6 hours: no leak |
| 3 | 39 week gestation. | Negative | Clinical observation: no leak |
| 4 | 40 week gestation. | Negative | Clinical observation: no leak |
| 5 | 39-40 week gestation. | Negative | Clinical observation: no leak |
| 6 | 39-40 week gestation. | Negative | Clinical observation: no leak |
| 7 | 39-40 week gestation. Cervical erosion | Negative | Clinical observation: no leak |
| 8 | 40 week gestation. Symptoms of labor. Amniotic fluid leak | Positive | Clinical observation: amniotic fluid leak |
| 9 | 39 week gestation. | Negative | Clinical observation: no leak |
| 10 | 39-40 week gestation. | Negative | Clinical observation: no leak |
| 11 | 39 week gestation. | Negative | Clinical observation: no leak |

TABLE 15

Trials of the device of the present invention (Lot C 98-0007) in the Third Maternity Hospital of Moscow, Russian Federation, Obstetrics and Gynecology Chair of the State Moscow University of Russia.

| N | Diagnosis | Amnisure results | Notes |
|---|---|---|---|
| 1 | 39 week gestation. Nephropathy. Hydramnion | Negative | Labor pains, labor activity developed in 4 hours. Evident leak observed |
| 2 | 41 week gestation. Edema | Negative | Clinical observation for 6 hours: no leak |
| 3 | 39-40 week gestation. Giant fetus. Symptoms of labor. Nephropathy | Negative | Clinical observation: no leak |
| 4 | 39-40 week gestation. | Negative | Clinical observation: no leak |
| 5 | 37-38 week gestation. Blood admixture. Hypertension | Negative | Clinical observation: no leak |
| 6 | 36 week gestation. Nephropathy | Negative | Clinical observation: no leak |
| 7 | 40 week gestation. Suspected leak | Positive | Clinical observation: leak. Labor developed in 30 min. |
| 8 | 39-40 week gestation. | Negative | Clinical observation: no amniotic fluid leak |
| 9 | 38-39 week gestation. | Negative | Clinical observation: no leak |
| 10 | 38 week gestation. | Negative | Clinical observation: no leak |
| 11 | 39 week gestation. Teenage parturient. | Negative | Clinical observation: no leak |
| 12 | 32 week gestation. Fetal Hypotrophy. | Negative | Clinical observation: no leak |
| 13 | 39-40 week gestation. Gestosis | Negative | Clinical observation: no leak |
| 14 | 24 week gestation. Threatened abortion | Negative | Clinical observation: no leak |

TABLE 15-continued

Trials of the device of the present invention (Lot C 98-0007) in the Third Maternity Hospital of Moscow, Russian Federation, Obstetrics and Gynecology Chair of the State Moscow University of Russia.

| N | Diagnosis | Amnisure results | Notes |
|---|---|---|---|
| 15 | 34-35 week gestation. Gestosis | Negative | Clinical observation: no leak |
| 16 | 33 week gestation. Edema | Negative | Clinical observation: no leak |
| 17 | 34-35 week gestation. Gestosis. | Negative | Clinical observation: no leak |
| 18 | 35-36 week gestation. Fetal Hypotrophy. | Negative | Clinical observation: no leak |
| 19 | 32 week gestation. Threatened abortion | Negative | Clinical observation: no leak |
| 20 | 38-39 week gestation. Suspicion of leak. Blood admixture in vaginal discharge | Negative | Clinical observation: no leak. Water broke in 10 hours, labor started |
| 21 | 40-41 week gestation. Symptoms of labor | Negative | Clinical observation: no leak |
| 22 | 25 week gestation. Threatened abortion | Negative | Clinical observation: no leak |
| 23 | 28 week gestation. Gestosis | Negative | Clinical observation: no leak |

Notes: The leak of amniotic fluid in Tables 13, 14, 15 was clinically assessed by the amount of vaginal discharge, and by ultrasonographic examination.

The extended clinical observation at negative test results was possible because the patients were hospitalized for treatment of concomitant diseases.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

TABLE 16

Deposited Microorganisms in the Russian National Collection of Industrial Microorganisms (VKPM) Depositary (1 Dorozhny proezd 1, Moscow 117545, Russia).

| Name | Date of deposit | Accession no. |
|---|---|---|
| Hybridoma Cell Lines N52 | May 22, 2003 | VKPM H-92 |
| Hybridoma Cell Lines N271 | May 22, 2003 | VKPM H-93 |
| Hybridoma Cell Lines N42 | May 22, 2003 | VKPM H-94 |

The invention claimed is:

1. A method of detecting amniotic fluid in a sample comprising a vaginal secretion of a pregnant woman using a combination of at least three PAMG-1-specific monoclonal antibodies, the method comprising:
(a) contacting said sample with said at least three PAMG-1-specific monoclonal antibodies,
wherein at least one antibody of the three has a lower PAMG-1 binding specificity than at least one other antibody of the three; and
wherein the binding specificity of each of said three antibodies and specific combination thereof are selected to detect PAMG-1 in the sample when present at least in a predefined threshold amount that is greater than the regular background level of PAMG-1 in vaginal secretions of pregnant women in the absence of amniotic fluid and less than the level present in amniotic fluid;
(b) detecting a PAMG-1/antibody complex; and
(c) determining that said sample contains amniotic fluid if said PAMG-1/antibody complex is detected in step (b).

2. The method of claim 1, wherein said monoclonal antibodies are selected from the group consisting of M271, produced by hybridoma N271, deposited with the Russian National Collection of Industrial Microorganisms (VKPM) Depository and assigned accession number VKPM-93; M52, produced by hybridoma N52, deposited with the VKPM and assigned accession number VKPM-92; and M42, produced by hybridoma N42, deposited with the VKPM and assigned accession number VKPM-94.

3. The method of claim 1, wherein said predefined threshold amount is in the range of 5 to 10 nanograms per milliliter.

4. The method of claim 1, wherein one of said monoclonal antibodies is bound to a marker.

5. The method of claim 4, wherein the marker is a dye particle.

6. The method of claim 1, wherein said antibodies are used in a strip device.

7. The method of claim 6, wherein said strip device comprises a detector section which is upstream from a capture section, wherein at least one of said PAMG-1 specific monoclonal antibodies is a mobilizable antibody present in the detector section, and the other at least two monoclonal antibodies of said at least three monoclonal antibodies are immobilized in the capture section; and
wherein said at least one antibody having a lower PAMG-1 binding specificity than at least one other antibody of the three is one of the at least two antibodies immobilized in the capture section.

8. The method of claim 7, wherein the mobilizable antibody in said detector section comprises a marker; and
wherein mobilization of said mobilizable antibody by a fluid sample introduced to the strip device permits binding of the mobilizable antibody to any PAMG-1 in the sample, and binding of the mobilizable antibody-PAMG-1 complex formed thereby to the immobilized antibodies in said capture section.

* * * * *